(12) United States Patent
Staid et al.

(10) Patent No.: US 10,363,061 B2
(45) Date of Patent: Jul. 30, 2019

(54) NOZZLE ASSEMBLIES FOR LIQUID JET SURGICAL INSTRUMENTS AND SURGICAL INSTRUMENTS FOR EMPLOYING THE NOZZLE ASSEMBLIES

(71) Applicant: HydroCision, Inc., Billerica, MA (US)

(72) Inventors: Kevin P. Staid, Lowell, MA (US); James J. Frassica, Chelmsford, MA (US); Ernest A. Dion, Danvers, MA (US); David P. Hesketh, Methuen, MA (US); Joseph A. Meranda, Haverhill, MA (US)

(73) Assignee: HydroCision, Inc., Billerica, MA (US)

( * ) Notice: Subject to any disclaimer, the term of this patent is extended or adjusted under 35 U.S.C. 154(b) by 131 days.

(21) Appl. No.: 15/444,084

(22) Filed: Feb. 27, 2017

(65) Prior Publication Data

US 2017/0258484 A1 Sep. 14, 2017

Related U.S. Application Data

(63) Continuation of application No. 10/544,015, filed as application No. PCT/US2004/002893 on Feb. 2, (Continued)

(51) Int. Cl.
*A61B 17/3203* (2006.01)
*A61B 17/32* (2006.01)
(Continued)

(52) U.S. Cl.
CPC .... *A61B 17/3203* (2013.01); *A61B 17/32002* (2013.01); *A61B 17/320016* (2013.01);
(Continued)

(58) Field of Classification Search
CPC . A61B 17/3203; A61B 1/00091; A61B 17/32; A61B 17/320016; A61B 17/32037; A61M 3/0279; A61M 3/0283
See application file for complete search history.

(56) References Cited

U.S. PATENT DOCUMENTS 1,889,425 A 11/1932 Sorenson
1,902,418 A 3/1933 Pilgrim
(Continued)

FOREIGN PATENT DOCUMENTS

DE 2 933 266 5/1981
DE 3 320 076 12/1984
(Continued)

OTHER PUBLICATIONS

Aeikens, B. "Cracking of Ureter Calculi by High Speed Water Jet Pulses," 8th International Symposium on Jet Cutting Technology, Paper 15, pp. 157/166. Sep. 9/11, 1986.
(Continued)

*Primary Examiner* — Katherine M Rodjom
(74) *Attorney, Agent, or Firm* — Knobbe, Martens, Olson & Bear LLP

(57) ABSTRACT

Disclosed are nozzles and nozzle assemblies of liquid jet-forming surgical instruments, surgical instruments employing such nozzles and/or nozzle assemblies, and methods of fabricating the nozzle assemblies in forming surgical instruments. Also, disclosed are liquid jet-forming surgical instruments including both liquid jet-forming nozzles and optional evacuation lumens, which when provided can be configured to receive the liquid jet and evacuate the liquid forming the liquid jet. Certain embodiments of such surgical instruments include inventive nozzle alignment component(s) to facilitate alignment of the nozzles and evacuation lumen upon assembly. In certain embodiments, surgical instruments are provided that include a nozzle that is shaped to form a liquid jet, which has surfaces that are optically smooth. In certain embodiments, the nozzle has a configuration enabling the nozzle to form a liquid jet that has the ability to remain collimated over longer distances than is typically achievable with conventional liquid jet surgical instrument nozzles
(Continued)

having the same ratio of nozzle length to minimum inner diameter of the jet opening. In certain embodiments, nozzle assemblies comprising an operative assembly of at least two subcomponents, which together provide a nozzle are provided. In certain embodiments, the at least two sub-components may comprise a nozzle-providing component, such as a nozzle ring, and a holder that is configured to retain and position the nozzle-providing component in the nozzle assembly. In certain embodiments, the nozzle-providing component can comprise a liquid flow passage having a diameter that continuously decreases along at least a portion of its length.

19 Claims, 5 Drawing Sheets

Related U.S. Application Data 2004, now Pat. No. 9,597,107, which is a continuation-in-part of application No. 10/695,632, filed on Oct. 27, 2003, now Pat. No. 8,162,966.

(60) Provisional application No. 60/488,024, filed on Jul. 17, 2003, provisional application No. 60/444,344, filed on Jan. 31, 2003, provisional application No. 60/421,219, filed on Oct. 25, 2002.

(51) Int. Cl.
A61M 1/00 (2006.01)
A61B 17/3207 (2006.01)
A61B 17/00 (2006.01)

(52) U.S. Cl.
CPC ..... *A61B 17/32037* (2013.01); *A61M 1/0084* (2013.01); *A61B 17/320708* (2013.01); *A61B 17/320783* (2013.01); *A61B 2017/00535* (2013.01)

(56) References Cited

U.S. PATENT DOCUMENTS

| | | |
|---|---|---|
| 2,429,356 A | 10/1947 | Hicks |
| 2,937,444 A | 5/1960 | Kern |
| 3,128,079 A | 4/1964 | De Groff |
| 3,210,848 A | 10/1965 | Bizzigotti |
| 3,565,062 A | 2/1971 | Kuris |
| 3,578,872 A | 5/1971 | McBurnie |
| 3,590,813 A | 7/1971 | Roszyk |
| 3,731,384 A | 5/1973 | Brooks et al. |
| 3,731,385 A | 5/1973 | Farber et al. |
| 3,818,913 A | 6/1974 | Wallach |
| 3,835,858 A | 9/1974 | Hagen |
| 3,844,272 A | 10/1974 | Banko |
| 3,906,954 A | 9/1975 | Baehr et al. |
| 3,930,505 A | 1/1976 | Wallach |
| 3,937,222 A | 2/1976 | Banko |
| 3,976,077 A | 8/1976 | Kerfoot, Jr. |
| 4,024,866 A | 5/1977 | Wallach |
| 4,061,146 A | 12/1977 | Baehr et al. |
| 4,111,490 A | 9/1978 | Liesveld |
| 4,137,804 A | 2/1979 | Gerber |
| 4,203,444 A | 5/1980 | Bonnell et al. |
| 4,229,139 A | 10/1980 | Marantette et al. |
| 4,235,595 A | 11/1980 | Arnegger |
| 4,245,624 A | 1/1981 | Komiya |
| 4,282,867 A | 8/1981 | Du Toit |
| 4,294,251 A | 10/1981 | Greenwald et al. |
| 4,320,761 A | 3/1982 | Haddad |
| 4,368,734 A | 1/1983 | Banko |
| 4,435,902 A | 3/1984 | Mercer et al. |
| 4,445,509 A | 5/1984 | Auth |
| 4,499,899 A | 2/1985 | Lyons, III |
| 4,512,344 A | 4/1985 | Barber |
| 4,517,977 A | 5/1985 | Frost |
| 4,522,206 A | 6/1985 | Whipple et al. |
| 4,545,374 A | 10/1985 | Jacobson |
| 4,560,373 A | 12/1985 | Sugino et al. |
| 4,583,531 A | 4/1986 | Mattchen |
| 4,589,412 A | 5/1986 | Kensey |
| 4,631,052 A | 12/1986 | Kensey |
| 4,637,551 A | 1/1987 | Seeger, Jr. et al. |
| 4,690,140 A | 9/1987 | Mecca |
| 4,690,672 A | 9/1987 | Veltrup |
| 4,694,828 A | 9/1987 | Eichenbaum |
| 4,705,038 A | 11/1987 | Sjostrom et al. |
| 4,715,848 A | 12/1987 | Beroza |
| 4,729,763 A | 3/1988 | Henrie |
| 4,735,604 A | 4/1988 | Watmough et al. |
| 4,735,620 A | 4/1988 | Ruiz |
| 4,747,821 A | 5/1988 | Kensey et al. |
| 4,749,376 A | 6/1988 | Kensey et al. |
| 4,770,174 A | 9/1988 | Luckman et al. |
| 4,790,813 A | 12/1988 | Kensey |
| 4,798,339 A | 1/1989 | Sugino et al. |
| 4,815,462 A | 3/1989 | Clark |
| 4,827,615 A | 5/1989 | Graham |
| 4,827,679 A | 5/1989 | Earle, III |
| 4,839,492 A | 6/1989 | Bouchier et al. |
| 4,842,578 A | 6/1989 | Johnson et al. |
| 4,898,574 A | 2/1990 | Uchiyama et al. |
| 4,913,698 A | 4/1990 | Ito et al. |
| 4,935,006 A | 6/1990 | Hasson |
| 4,937,985 A | 7/1990 | Boers et al. |
| 4,986,807 A | 1/1991 | Farr |
| 5,002,546 A | 3/1991 | Romano |
| 5,018,670 A | 5/1991 | Chalmers |
| 5,027,792 A | 7/1991 | Meyer |
| 5,037,431 A | 8/1991 | Summers et al. |
| 5,037,432 A | 8/1991 | Molinari |
| 5,042,984 A | 8/1991 | Kensey et al. |
| 5,052,624 A | 10/1991 | Boers et al. |
| 5,057,098 A | 10/1991 | Zelman |
| 5,074,862 A | 12/1991 | Rausis |
| 5,097,849 A | 3/1992 | Kensey et al. |
| 5,111,652 A | 5/1992 | Andre |
| 5,112,299 A | 5/1992 | Pascaloff |
| 5,114,399 A | 5/1992 | Kovalcheck |
| 5,125,582 A | 6/1992 | Surjaatmadja et al. |
| 5,135,482 A | 8/1992 | Neracher |
| 5,135,484 A | 8/1992 | Wright |
| 5,162,016 A | 11/1992 | Malloy |
| 5,186,714 A | 2/1993 | Boudreault et al. |
| 5,195,958 A | 3/1993 | Phillips |
| 5,195,959 A | 3/1993 | Smith |
| 5,205,779 A | 4/1993 | O'Brien |
| 5,217,465 A | 6/1993 | Steppe |
| 5,230,704 A | 7/1993 | Moberg |
| 5,242,449 A | 9/1993 | Zaleski |
| 5,250,065 A | 10/1993 | Clement et al. |
| 5,254,117 A | 10/1993 | Rigby et al. |
| 5,255,017 A | 10/1993 | Lam |
| 5,259,842 A | 11/1993 | Plechinger et al. |
| 5,275,607 A | 1/1994 | Lo et al. |
| 5,286,253 A | 2/1994 | Fucci |
| RE34,556 E | 3/1994 | Sjostrom et al. |
| 5,300,022 A | 4/1994 | Klapper et al. |
| 5,312,400 A | 5/1994 | Bales et al. |
| 5,314,375 A | 5/1994 | O'Brien et al. |
| 5,314,406 A | 5/1994 | Arias et al. |
| 5,318,518 A | 6/1994 | Plechinger et al. |
| 5,320,599 A | 6/1994 | Griep et al. |
| 5,322,504 A | 6/1994 | Doherty et al. |
| 5,339,799 A | 8/1994 | Kami et al. |
| 5,348,555 A | 9/1994 | Zinnanti |
| 5,350,390 A | 9/1994 | Sher |
| 5,364,395 A | 11/1994 | West, Jr. |
| 5,370,609 A | 12/1994 | Drasler et al. |
| 5,383,876 A | 1/1995 | Nardella |
| 5,395,312 A | 3/1995 | Desai |
| 5,395,315 A | 3/1995 | Griep |

(56) References Cited

U.S. PATENT DOCUMENTS

| | | |
|---|---|---|
| 5,395,369 A | 3/1995 | McBrayer et al. |
| 5,409,376 A | 4/1995 | Murphy |
| 5,429,596 A | 7/1995 | Arias et al. |
| 5,437,662 A | 8/1995 | Nardella |
| 5,441,482 A | 8/1995 | Clague et al. |
| 5,441,499 A | 8/1995 | Fritzsch |
| 5,449,357 A | 9/1995 | Zinnanti |
| 5,449,369 A | 9/1995 | Imran |
| 5,451,223 A | 9/1995 | Ben/Simhon |
| 5,453,088 A | 9/1995 | Boudewijn et al. |
| 5,454,827 A | 10/1995 | Aust et al. |
| 5,468,028 A | 11/1995 | Olson |
| 5,476,450 A | 12/1995 | Ruggio |
| 5,484,441 A | 1/1996 | Koros et al. |
| 5,496,267 A | 3/1996 | Drasler et al. |
| 5,505,729 A | 4/1996 | Rau |
| 5,512,044 A | 4/1996 | Duer |
| 5,520,685 A | 5/1996 | Wojciechowicz |
| 5,524,821 A | 6/1996 | Yie et al. |
| 5,527,330 A | 6/1996 | Tovey |
| 5,527,331 A | 6/1996 | Kresch et al. |
| 5,527,332 A | 6/1996 | Clement |
| 5,549,606 A | 8/1996 | McBrayer et al. |
| 5,551,448 A | 9/1996 | Matula et al. |
| 5,554,112 A | 9/1996 | Walbrink et al. |
| 5,556,406 A | 9/1996 | Gordon et al. |
| 5,562,640 A | 10/1996 | McCabe et al. |
| 5,562,692 A | 10/1996 | Bair |
| 5,569,258 A | 10/1996 | Gambale |
| 5,584,855 A | 12/1996 | Onik |
| 5,591,184 A | 1/1997 | McDonnell et al. |
| 5,607,391 A | 3/1997 | Klinger et al. |
| 5,609,573 A | 3/1997 | Sandock |
| 5,618,293 A | 4/1997 | Sample et al. |
| 5,620,414 A | 4/1997 | Campbell, Jr. |
| 5,643,299 A | 7/1997 | Bair |
| 5,653,713 A | 8/1997 | Michelson |
| 5,658,249 A | 8/1997 | Beland et al. |
| 5,662,680 A | 9/1997 | Desai |
| 5,667,480 A | 9/1997 | Knight et al. |
| 5,672,945 A | 9/1997 | Krause |
| 5,674,226 A | 10/1997 | Doherty et al. |
| 5,683,366 A | 11/1997 | Eggers et al. |
| 5,685,840 A | 11/1997 | Schechter et al. |
| 5,685,877 A | 11/1997 | Pagedas et al. |
| 5,688,269 A | 11/1997 | Newton et al. |
| 5,697,281 A | 12/1997 | Eggers et al. |
| 5,697,536 A | 12/1997 | Eggers et al. |
| 5,697,882 A | 12/1997 | Eggers et al. |
| 5,702,387 A | 12/1997 | Arts et al. |
| 5,709,697 A | 1/1998 | Ratcliff et al. |
| 5,713,849 A | 2/1998 | Bosma et al. |
| 5,713,851 A | 2/1998 | Boudewijn |
| 5,713,878 A | 2/1998 | Moutafis et al. |
| 5,730,742 A | 3/1998 | Wojciechowicz |
| 5,735,815 A | 4/1998 | Bair |
| 5,749,885 A | 5/1998 | Sjostrom et al. |
| 5,766,167 A | 6/1998 | Eggers et al. |
| 5,766,177 A | 6/1998 | Lucas/Dean et al. |
| 5,779,713 A | 7/1998 | Turjanski et al. |
| 5,782,795 A | 7/1998 | Bays |
| 5,782,829 A | 7/1998 | Swiantek et al. |
| 5,785,675 A | 7/1998 | Drasler et al. |
| 5,788,667 A | 8/1998 | Stoller |
| 5,792,139 A | 8/1998 | Chambers |
| 5,792,167 A | 8/1998 | Kablik et al. |
| 5,797,907 A | 8/1998 | Clement |
| 5,803,733 A | 9/1998 | Trott et al. |
| 5,810,809 A | 9/1998 | Rydell |
| 5,827,323 A | 10/1998 | Klieman et al. |
| 5,830,214 A | 11/1998 | Flom et al. |
| 5,843,017 A | 12/1998 | Yoon |
| 5,843,021 A | 12/1998 | Edwards et al. |
| 5,849,023 A | 12/1998 | Mericle |
| 5,851,214 A | 12/1998 | Larsen et al. |
| 5,853,384 A | 12/1998 | Blair |
| 5,861,002 A | 1/1999 | Desai |
| 5,868,742 A | 2/1999 | Manes et al. |
| 5,868,785 A | 2/1999 | Tal et al. |
| 5,871,462 A | 2/1999 | Yoder et al. |
| 5,879,358 A | 3/1999 | Semm |
| 5,891,086 A * | 4/1999 | Weston ............... A61M 5/30 604/143 |
| 5,899,915 A | 5/1999 | Saadat |
| 5,904,681 A | 5/1999 | West, Jr. |
| 5,913,867 A | 6/1999 | Dion |
| 5,927,976 A | 7/1999 | Wu |
| 5,941,876 A | 8/1999 | Nardella et al. |
| 5,941,893 A | 8/1999 | Saadat |
| 5,944,686 A | 8/1999 | Patterson et al. |
| 5,947,988 A | 9/1999 | Smith |
| 5,961,531 A | 10/1999 | Weber |
| 6,007,533 A | 12/1999 | Casscells |
| 6,013,076 A | 1/2000 | Goble et al. |
| 6,017,354 A | 1/2000 | Culp et al. |
| 6,036,698 A | 3/2000 | Fawzi et al. |
| 6,045,564 A | 4/2000 | Walen |
| 6,053,923 A | 4/2000 | Veca et al. |
| 6,066,150 A | 5/2000 | Gonon |
| 6,083,189 A | 7/2000 | Gonon et al. |
| 6,096,001 A | 8/2000 | Drasler et al. |
| 6,099,514 A | 8/2000 | Sharkey et al. |
| 6,110,169 A | 8/2000 | Mueller et al. |
| 6,129,740 A | 10/2000 | Michelson |
| 6,135,977 A | 10/2000 | Drasler et al. |
| 6,142,997 A | 11/2000 | Michelson |
| 6,149,622 A | 11/2000 | Marie |
| 6,200,320 B1 | 3/2001 | Michelson |
| 6,206,898 B1 | 3/2001 | Honeycutt et al. |
| 6,214,010 B1 | 4/2001 | Farley et al. |
| 6,216,573 B1 | 4/2001 | Moutafis et al. |
| 6,280,302 B1 | 8/2001 | Hashish et al. |
| 6,322,533 B1 | 11/2001 | Gonon |
| 6,375,635 B1 | 4/2002 | Moutafis et al. |
| 6,402,715 B2 | 6/2002 | Manhes |
| 6,419,654 B1 | 7/2002 | Kadan |
| 6,423,028 B1 | 7/2002 | Gonon |
| 6,451,017 B1 | 9/2002 | Moutafis et al. |
| 6,464,567 B2 | 10/2002 | Hashish et al. |
| 6,491,660 B2 | 12/2002 | Guo et al. |
| 6,508,823 B1 | 1/2003 | Gonon |
| 6,511,493 B1 | 1/2003 | Moutafis et al. |
| 6,544,220 B2 | 4/2003 | Shuman et al. |
| 6,669,710 B2 | 12/2003 | Moutafis et al. |
| 6,899,712 B2 | 5/2005 | Moutafis et al. |
| 6,923,792 B2 | 8/2005 | Staid et al. |
| 6,960,182 B2 | 11/2005 | Moutafis et al. |
| 7,122,017 B2 | 10/2006 | Moutafis et al. |
| 8,162,966 B2 | 4/2012 | Connor et al. |
| 8,529,498 B2 | 9/2013 | Moutafis |
| 8,851,866 B2 | 10/2014 | Moutafis |
| 9,597,107 B2 * | 3/2017 | Staid ............ A61B 17/320016 |
| 2001/0002562 A1 | 6/2001 | Moutafis et al. |
| 2002/0111579 A1 | 8/2002 | Moutafis et al. |
| 2002/0176788 A1 | 11/2002 | Moutafis et al. |
| 2002/0177802 A1 | 11/2002 | Moutafis et al. |
| 2003/0009166 A1 | 1/2003 | Moutafis et al. |
| 2003/0055404 A1 | 3/2003 | Moutafis |
| 2003/0083681 A1 | 5/2003 | Moutafis et al. |
| 2003/0088259 A1 | 5/2003 | Staid et al. |
| 2003/0125660 A1* | 7/2003 | Moutafis ............ A61B 17/3203 604/22 |
| 2004/0228736 A1 | 11/2004 | Moutafis et al. |
| 2004/0230211 A1 | 11/2004 | Moutafis et al. |
| 2004/0234380 A1 | 11/2004 | Moutafis et al. |
| 2004/0243157 A1 | 12/2004 | Connor |
| 2005/0159765 A1 | 7/2005 | Moutafis et al. |
| 2005/0267443 A1 | 12/2005 | Staid et al. |
| 2005/0283150 A1 | 12/2005 | Moutafis et al. |
| 2006/0229550 A1 | 10/2006 | Staid et al. |
| 2006/0264808 A1 | 11/2006 | Frassica et al. |

(56) References Cited

U.S. PATENT DOCUMENTS

FOREIGN PATENT DOCUMENTS

| | | |
|---|---|---|
| DE | 3 421 390 | 12/1985 |
| DE | 40 18 736 | 1/1992 |
| DE | 197 34 890 | 7/1999 |
| EP | 0 175 096 | 3/1986 |
| EP | 0 253 478 | 1/1988 |
| EP | 0 258 901 | 3/1988 |
| EP | 0 280 972 | 9/1988 |
| EP | 0 335 861 | 10/1989 |
| EP | 0 367 855 | 5/1990 |
| EP | 0 411 170 | 2/1991 |
| EP | 0 442 579 | 8/1991 |
| EP | 0 470 781 | 2/1992 |
| EP | 0 485 133 | 5/1992 |
| EP | 0 489 496 | 6/1992 |
| EP | 0 527 312 | 6/1992 |
| EP | 0 551 920 | 7/1993 |
| EP | 0 555 549 | 8/1993 |
| EP | 0 620 016 | 10/1994 |
| EP | 0 636 345 | 2/1995 |
| EP | 0 637 453 | 2/1995 |
| EP | 0 693 295 | 1/1996 |
| EP | 0 737 450 | 10/1996 |
| EP | 0 771 176 | 5/1997 |
| EP | 0 806 213 | 11/1997 |
| EP | 1 025 807 | 8/2000 |
| FR | 2 779 934 | 12/1999 |
| FR | 2 779 935 | 12/1999 |
| JP | H5-193143 | 8/1993 |
| JP | H6-240488 | 8/1994 |
| JP | H9-122133 | 5/1997 |
| SU | 753434 | 2/1978 |
| WO | WO 1990/05493 | 5/1990 |
| WO | WO 1994/10917 | 5/1994 |
| WO | WO 1994/28807 | 12/1994 |
| WO | WO 1996/24299 | 8/1996 |
| WO | WO 1996/39914 | 12/1996 |
| WO | WO 1996/39954 | 12/1996 |
| WO | WO 1996/40476 | 12/1996 |
| WO | WO 1997/00647 | 1/1997 |
| WO | WO 1997/03713 | 2/1997 |
| WO | WO 1997/24074 | 10/1997 |
| WO | WO 1997/48345 | 12/1997 |
| WO | WO 1997/49441 | 12/1997 |
| WO | WO 1999/33510 | 7/1999 |
| WO | WO 1999/65407 | 12/1999 |
| WO | WO 1999/65408 | 12/1999 |
| WO | WO 1999/66848 | 12/1999 |
| WO | WO 2000/69348 | 11/2000 |
| WO | WO 2001/22890 | 4/2001 |
| WO | WO 2001/50965 | 7/2001 |
| WO | WO 2001/50966 | 7/2001 |
| WO | WO 2002/095234 | 11/2002 |
| WO | WO 2003/013645 | 2/2003 |
| WO | WO 2003/024340 | 3/2003 |
| WO | WO 2003/045259 | 6/2003 |
| WO | WO 2004/069064 | 8/2004 |
| WO | WO 2004/037095 | 9/2004 |
| WO | WO 2006/066160 | 6/2006 |

OTHER PUBLICATIONS

Baer et al., "Jet-Cutting—An Alternative to the Ultrasonic Aspirator?" Chirurg, 61:735, 1990 and Reply to commentary.
Baer et al., "Hepatic Surgery Facilitated by a New Jet Dissector," HPB Surgery, vol. 4, pp. 137/146, 1991.
Baer et al., "New water-jet dissector: initial experience in hepatic surgery," Br. J. Surg., vol. 78, pp. 502/503, Apr. 1991.
Baer et al., "Subtotal hepatectomy: a new procedure based on the inferior right hepatic vein," Br. J. Surg., vol. 78, pp. 1221/1222, Oct. 1991.
Baer et al., "Water-jet dissection in hepatic surgery," Minimally Invasive Therapy, vol. 1, pp. 169/172, 1992.
Balje, O.E. et al., "Turbomechanies: A Guide to Design, Selection, and Theory," John Wiley & Sons Publisher, Chap. 5, Sect. 3, pp. 252/259, 1981.
Beard, J. "Water jet puts surgeons at the cutting edge," New Scientist, Jul. 23, 1994.
Bucker et al., "Comparative in Vitro Study of Two Percutaneous Hydrodynamic Thrombectomy Systems," Journal of Vascular and Interventional Radiology, vol. 7, No. 3, pp. 445/449, May/Jun. 1996.
Communication issued in European Application No. 04 707 378.8-2310, dated Oct. 1, 2009.
Communication issued in European Application No. 03 809 652.5-2310, dated Nov. 20, 2008.
Douek et al., "Functional Properties of a Prototype Rheolytic Catheter for Percutaneous Thrombectomy In Vitro Investigations," Investigative Radiology, vol. 29, No. 5, pp. 547/552, 1994.
Drasler et al., "A Rheolytic System for Percutaneous Coronary and Peripheral Plaque Removal," Angiology/The Journal of Vascular Diseases, vol. 42, No. 2, pp. 90/98, Feb. 1991.
Drasler et al., "Rheolytic Catheter for Percutaneous Removal of Thrombus," Radiology, vol. 182, pp. 263/267, Jan. 1992.
Examiner's Report issued in Australian Application No. 2003301525, dated Sep. 15, 2008.
Examiner's Report issued in Australian Application No. 2004209990, dated Feb. 16, 2009.
Field, J.E. "The physics of liquid impact, shock wave interactions with cavities, and the implications to shock wave lithotripsy," Phys. Med. Bio., vol. 36, No. 11, pp. 1475/1484, 1991.
Giraud et al., "Bone cutting," Clin. Phys. Physiol. Meas., vol. 12, No. 1, pp. 1/19, 1991.
Hata et al., "Liver Resection in Children, Using a Water/Jet," Journal of Pediatric Surgery, vol. 29, No. 5, pp. 648/650, May 1994.
International Search Report, re PCT Application No. PCT/US2004/002893, dated Nov. 8, 2004.
International Preliminary Report on Patentability, re PCT Application No. PCT/US2004/002893, dated Aug. 5, 2005.
International Search Report, re PCT Application No. PCT/US2003/034174, dated Jul. 16, 2004.
Izumi et al., "Hepatic Resection Using a Water Jet Dissector," Surgery Today Jpn. J. Surg., vol. 23. pp. 31/35, 1993.
Jessen et al., "Endoscopic Jet Cutting of Human Gallstones," 7th Internal Symposium on Jet Cutting Technology, Paper D4, pp. 211/220, Jun. 26/28, 1984.
Jessen, K. et al., "Endoscopic Jet-Cutting A New Method for Stone Destruction in the Common Bile Duct," 6th Internal Symposium on Jet Cutting Technology, Paper B1, pp. 39/52, Apr. 6/8, 1982.
Kobayashi et al., "Experimental Study of Water Jet Angioplasty," Vascular Surgery—International Conference, Oct. 1993, vol. 2, pp. 626/631.
Müller-Hülsbeck, S. et al., "Rhetolytic Thrombectomy of an Acutely Thrombosed Transjugular Intrahepatic Portosystemic Stent Shunt," Cardio Vasc. Intervent. Radiol., vol. 19, pp. 294/297, 1996.
Office Action issued in Japanese Application No. 2006-503244, dated Sep. 16, 2009.
Office Action issued in Japanese Application No. 2006-503244, dated Oct. 2010.
Office Action issued in Japanese Application No. 2005-501705, dated Sep. 11, 2009.
Orthopedic Sourcebook, "Instruments for Surgeons," Kmedic, 1999.
Overbosch, E.H. et al., "Occluded Hemodialysis Shunts: Dutch Multicenter Experience with the Hydrolyser Catheter," Radiology, vol. 201, No. 2, pp. 485/488, 1996.
Papachristou et al., "Resection of the liver with a water jet," Br. J. Surg., vol. 69, pp. 93/94, 1982.
Persson et al., "Transection of the Liver with a Water Jet," Surgery, Gynecology & Obstetrics, vol. 168, pp. 267/268, Mar. 1989.
Reekers, J.A. et al., "Catheter for Percutaneous Thrombectomy: First Clinical Experience," Radiology, vol. 188, No. 3, pp. 871/874, 1993.
Schob et al., "The Multimodal Water Jet Dissector—A Technology for Laparoscopic Liver Surgery," End. Surg., vol. 2, pp. 311/314, 1994.

(56) References Cited

OTHER PUBLICATIONS

Schob, O.M. et al., "Experimental laprascopic liver resection with a multimodal water jet dissector," British Journal of Surgery, vol. 82, pp. 392/393, 1995.

Shimi, S.M. "Dissection techniques in laparoscopic surgery: a review," J.R. Coll. Surg. Edinb., vol. 40, pp. 249/259, Aug. 1995.

Spence, R.K. "Emerging Trends in Surgical Blood Transfusion," Seminars in Hematology, vol. 34, No. 3, Suppl 2, pp. 48/53, Jul. 1997.

Summers, D.A. and J. Viebrock, "The Impact of Waterjets on Human Flesh," 9th International Symposium on Jet Cutting Technology, Paper H4, pp. 423/433, Oct. 4/6, 1988.

Terzis, A.J.A. et al., "A New System for Cutting Brain Tissue Preserving Vessels: water jet cutting," British Journal of Neurosurgery, vol. 3, pp. 361/366, 1989.

The Anspach Effort Inc. "Black Max" 2 pgs printed from www.anspach.com/blackmax.php, Oct. 28, 2003.

The Anspach Effort Inc. "Micro Max" 2 pgs printed from www.anspach.com/micromax.php, Oct. 28, 2003.

The Anspach Effort Inc, "Micro Max plus" 2 pgs printed from www.anspach.com/micromax_plus.php, Oct. 28, 2003.

The Anspach Effort Inc, "E Max" 3 pgs printed from www.anspach.com/emax.php, Oct. 28, 2003.

The Anspach Effort Inc. "Black Max Attachments Accessories" 8 pgs printed from www.anspach.com/blackmaxattach.php, Oct. 28, 2003.

The Anspach Effort Inc. "Universal Attachments Accessories" 3 pgs printed from www.anspach.com/universal_attachments.php, Oct. 28, 2003.

Truchot, P. et al., "Development of a Cryogenic Waterjet Technique for Biomaterial Processing Applications," 6th American Water Jet Conference, Paper 35, pp. 473/480, Aug. 24/27, 1991.

Uchino, J. et al., "Surgical Cutting of the Liver by Water Jet," 9th International Symposium on Jet Cutting Technology, Poster 1, pp. 629/639, Oct. 4/6, 1988.

Van Ommen, V.G. et al., "Removal of Thrombus from Aortocornary Bypass Grafts and Coronary Arteries Using the 6Fr Hydrolyser," The American Journal of Cardiology, vol. 79, pp. 1012/1016, Apr. 1997.

Vijay, M.M. "A Critical Examination of the Use of Water Jets for Medical Applications," 5th American Water Jet Conference, Paper/Communication 42, pp. 425/448, Aug. 29/31, 1989.

Water Jet Dissector, Hepatotom® Supersonic Microjet Dissector brochure, Medical Exports AG.

Wilson et al., The Design of High-Efficiency Turbomachinery and Gas Turbines, Prentice Hall Publisher, 2nd edition, pp. 31, 1998.

Zhong, P. et al., "Propagation of shock waves in elastic solids caused by cavitation microjet impact. II: Application in extracorporeal shock wave lithotripsy," J. Acoust. Soc. Am., vol. 94, No. 1, pp. 29/36, Jul. 1993.

Canadian Office Action, re CA Application No. 2,554,930, dated Jul. 5, 2011.

International Written Opinion, re PCT Application No. PCT/US2004/002893, dated Jul. 31, 2005.

\* cited by examiner

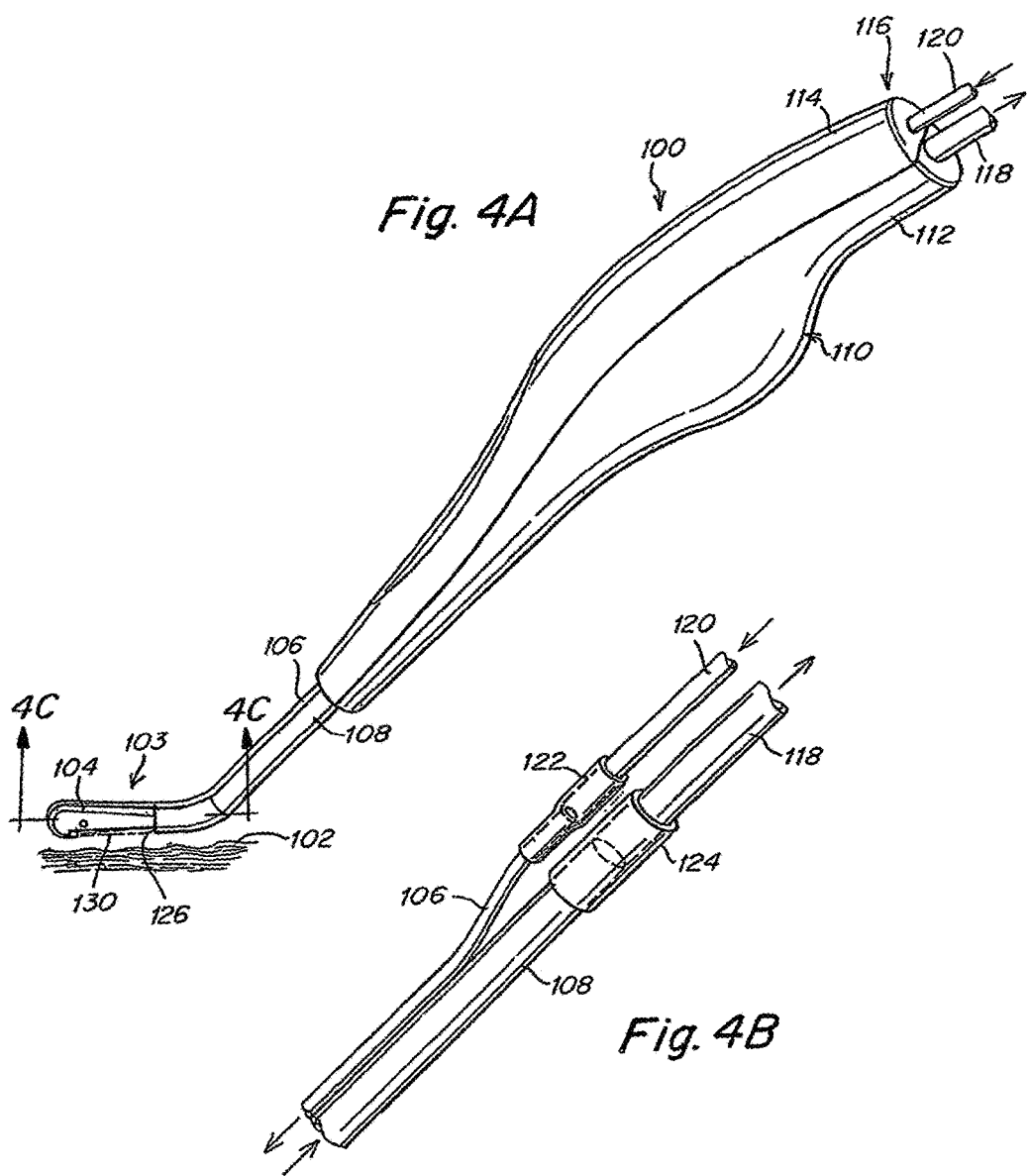

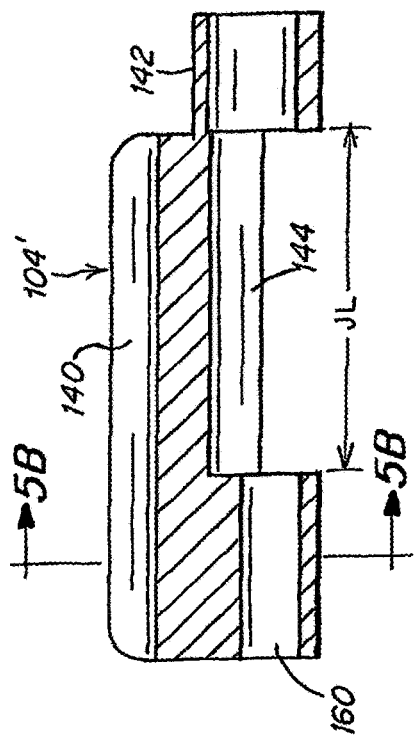
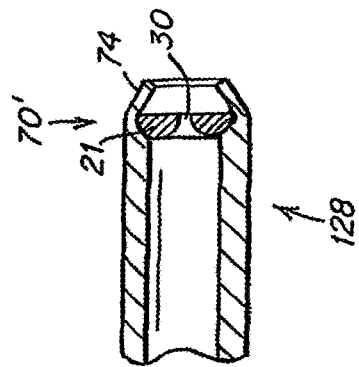
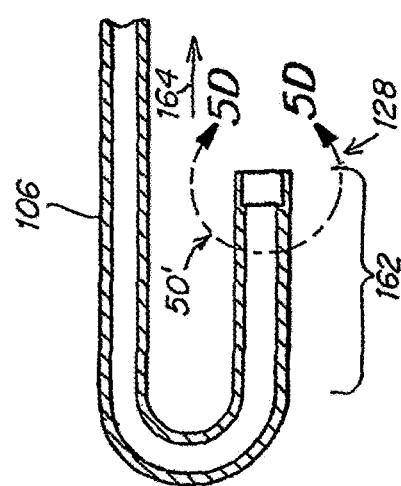
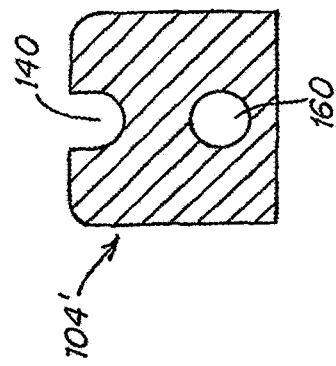

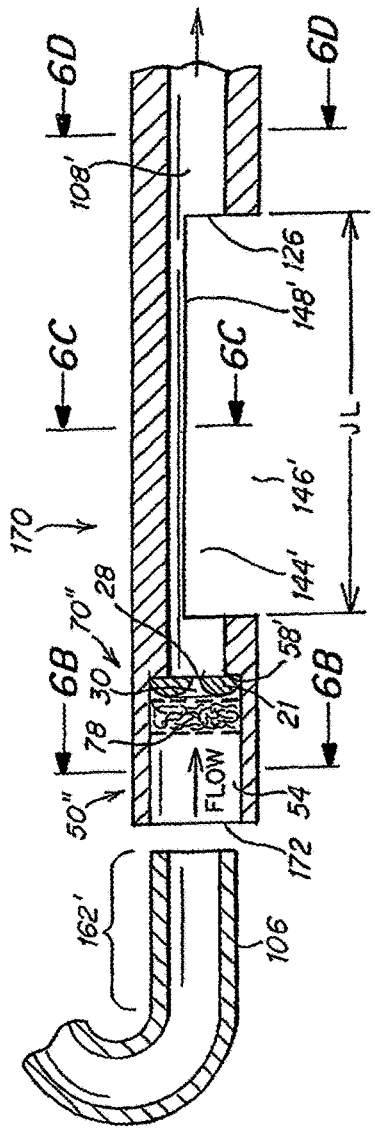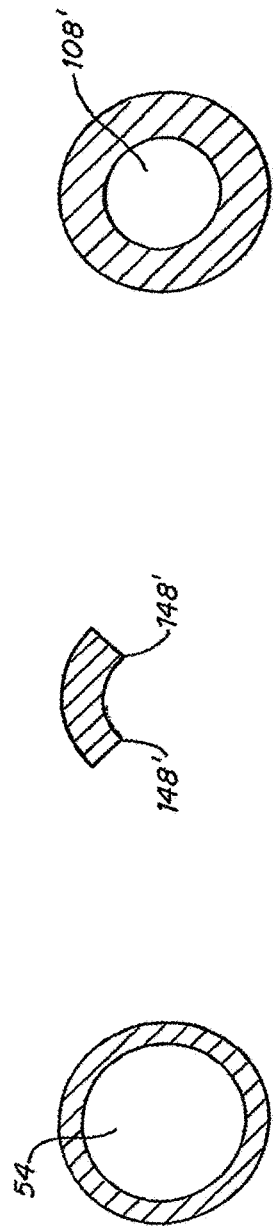
Fig. 6A
Fig. 6B
Fig. 6C
Fig. 6D

NOZZLE ASSEMBLIES FOR LIQUID JET SURGICAL INSTRUMENTS AND SURGICAL INSTRUMENTS FOR EMPLOYING THE NOZZLE ASSEMBLIES

CROSS REFERENCE TO RELATED APPLICATIONS

This application is a continuation of U.S. patent application Ser. No. 10/544,015, filed on Mar. 31, 2006 and issued as U.S. Pat. No. 9,597,107, which is a continuation-in-part of U.S. patent application Ser. No. 10/695,632, filed on Oct. 27, 2003 and issued as U.S. Pat. No. 8,162,966, which claims the benefit of U.S. Provisional Patent Application No. 60/488,024, filed on Jul. 17, 2003, U.S. Provisional Patent Application No. 60/421,219, filed on Oct. 25, 2002, and U.S. Provisional Patent Application No. 60/444,344, filed on Jan. 31, 2003. The disclosures of these prior applications are incorporated by reference in their entirety.

BACKGROUND

1. Field of the Invention

This invention relates to nozzle assemblies for liquid jet-forming surgical instruments, surgical instruments employing the nozzle assemblies, and methods of fabricating such surgical instruments.

2. Description of the Related Art

Traditionally, many surgical procedures for both open surgery and minimally invasive surgery (i.e., endoscopic, laparoscopic, or arthroscopic surgical procedures) have utilized surgical tools such as scalpels, scrapers, blunt dissectors, lasers, electrosurgical devices, etc., which can have poor tissue differentiating capability, which may easily cause inadvertent damage to tissue surrounding a surgical treatment site, and which do not typically provide for an ability to precisely control a depth of cutting and/or tissue ablation with the instrument and/or effectively provide for evacuation from the treatment site of cut/ablated tissue. Many such surgical procedures can entail more extensive trauma to the patient and/or require longer operating procedures, with associated problems of long recovery periods and potential complication, than is desirable.

Instruments that employ liquid jets have also been utilized in surgical procedures for cutting and ablating tissue. Such instruments can have certain advantages over the above-mentioned traditional surgical instruments for performing surgical and medical procedures. For example, the cutting or ablating power of the liquid jet may be adjusted or controlled by an operator of the instrument, for example by varying the pressure of the liquid supplied to form the jet, to allow for improved tissue differentiation and to reduce inadvertent damage to surrounding tissues when cutting or ablating the target tissue. When operated at lower liquid pressures, the instruments can be utilized for lavage and/or debridement of tissue, without substantial cutting. A variety of such liquid jet surgical instruments for performing open surgical procedures, minimally invasive surgical procedures, and surgical procedures performed on an external portion of the body of a patient (e.g., wound cleansing or skin debridement) are known in the art. Several such instruments are described in commonly-owned U.S. Pat. No. 5,944,686, issued Aug. 31, 1999, U.S. Pat. No. 6,375,635, issued Apr. 23, 2002, and U.S. Pat. No. 6,511,493, issued Sep. 17, 2002, each incorporated herein by reference, and in commonly-owned published U.S. Patent Publication No. 2003/0125660 A1, published Jul. 3, 2003, which is incorporated herein by reference.

Typically, many of the above-described surgical instruments are designed an supplied to be disposable after a single use. As described in the above-identified patents and published application, many liquid jet-forming surgical instruments utilize liquid pressures in excess of 1,000 psig, often in the range of between about 5,000 to 20,000 psig, and in some cases up to 50,000 psig or more. Typical nozzle internal diameters can range from about 0.001 to 0.02 inch. In forming such instruments, the ability to fabricate liquid jet-forming nozzles able to withstand such pressures while forming collimated jets is difficult. Moreover, because, as mentioned above, many such instruments are disposable after a single use, the ability to form nozzles in expensively and reproducibly in quantity adds to the difficulty. Typical nozzle assemblies for forming collimated jets for liquid jet-forming devices can tend to be expensive to fabricate and/or difficult to fabricate in bulk quantities reproducibly and/or can have relatively large ratios of nozzle length to diameter, which can lead to undesirably large pressure drops. Many conventional methods for making such small nozzle openings, such as electric discharge machining, microdrilling, and the like, tend to be expensive, relatively slow, and difficult to automate. In addition, facilitating alignment between liquid jet nozzles and jet receivers in such instruments during fabrication, especially for instruments having relatively long jet lengths, e.g. greater than 5 mm can be difficult.

While many of the above-mentioned surgical instruments, and especially liquid jet-based surgical instruments have utility for performing such surgical and medical procedures, there for improved nozzles and nozzle assemblies for liquid jet-based surgical instruments and for improved techniques and components for aligning liquid jet-forming nozzles in such instruments. The present invention provides, in certain embodiments, such improved nozzles, nozzle assemblies, and surgical liquid jet instruments, and further provides methods for their construction and use in a variety of surgical procedures.

SUMMARY

Disclosed are nozzles and nozzle assemblies of liquid jet-forming surgical instruments, surgical instruments employing such nozzles and/or nozzle assemblies, and methods of fabricating the nozzle assemblies in forming surgical instruments. Also, disclosed are liquid jet-forming surgical instruments including both liquid jet-forming nozzles and optional evacuation lumens, which when provided can be configured to receive the liquid jet and evacuate the liquid forming the liquid jet. Certain embodiments of such surgical instruments include inventive nozzle alignment component(s) to facilitate alignment of the nozzles and evacuation lumen upon assembly. In certain embodiments, surgical instruments are provided that include a nozzle that is shaped to form a liquid jet, which has surfaces that are optically smooth. In certain embodiments, the nozzle has a configuration enabling the nozzle to form a liquid jet that has the ability to remain collimated over longer distances than is typically achievable with conventional liquid jet surgical instrument nozzles having the same ratio of nozzle length to minimum inner diameter of the jet opening. In certain embodiments, nozzle assemblies comprising an operative assembly of at least two sub-components, which together provide a nozzle are provided. In certain embodiments, the at least two sub-components may comprise a nozzle-providing component, such as a nozzle ring, and a holder that is configured to retain and position the nozzle-providing component in the nozzle assembly. In certain embodiments, the nozzle-providing component can comprise a liquid flow passage having a diameter that continuously decreases along at least a portion of its length.

In one aspect, the invention is directed to surgical instruments. In one series of embodiments, surgical instruments comprising a nozzle assembly comprising a nozzle-providing component that is shaped to form a liquid jet; and a pressure lumen configured and positioned to convey a flow of liquid to the nozzle assembly; wherein the nozzle assembly comprises a holder that is configured to retain and position the nozzle-providing component, and wherein the nozzle-providing component comprises a liquid flow passage having a diameter that continuously decreases along at least a portion of a liquid flow path through the liquid flow passage are disclosed.

In another series of embodiments, surgical instruments comprising a nozzle assembly comprising a nozzle-providing component that is shaped to form a liquid jet; and a pressure lumen configured and positioned to convey a flow of liquid to the nozzle assembly; wherein the nozzle assembly comprises a holder that is configured to retain and position the nozzle-providing component; and wherein the holder comprises a recessed well having a seating surface comprising a hole, which hole is in fluid communication with the pressure lumen, the hole having an inner diameter less than an outer diameter of the nozzle-providing component when the nozzle-providing component is contained within the recessed well of the holder, and wherein the recessed well of the holder has an inner diameter at least as great as the outer diameter of the nozzle-providing component when the nozzle-providing component is contained within the recessed well of the holder are disclosed.

In another series of embodiments, surgical instruments comprising a nozzle assembly comprising a nozzle-providing component that is shaped to form a liquid jet; and a pressure lumen configured and positioned to convey a flow of liquid to the nozzle assembly; wherein the nozzle assembly comprises a holder that is configured to retain and position the nozzle-providing component, the holder comprising a recessed well formed in the distal tip of the pressure lumen are disclosed.

In another series of embodiments, surgical instruments comprising a nozzle assembly comprising a nozzle-providing component that is shaped to form a liquid jet; and a pressure lumen configured and positioned to convey a flow of liquid to the nozzle assembly; wherein the nozzle-providing component comprises a ring having an outer diameter not greater than 0.1 inch and a height, as measured in a direction parallel to the longitudinal axis of a hole defining a liquid flow path through the ring, less than the outer diameter are disclosed.

In another series of embodiments, surgical instruments comprising a nozzle that is shaped to form a liquid jet; and a pressure lumen configured and positioned to convey a flow of liquid to the nozzle; wherein the nozzle comprises a hole, defining a liquid flow path through the nozzle, which has surfaces that are optically smooth are disclosed.

In another series of embodiments, surgical instruments comprising a nozzle that is shaped to form a liquid jet; and a pressure lumen configured and positioned to convey a flow of liquid to the nozzle; wherein a ratio of a liquid flow path length through the nozzle to a minimum inner diameter of a jet-forming orifice of the nozzle does not exceed 4; and wherein the liquid jet formed by the instrument when in operation has a cone angle not exceeding 10 degrees are disclosed.

In another series of embodiments, surgical instruments comprising a pressure lumen configured and positioned to convey a flow of liquid comprising at or near its distal end a nozzle that is shaped to form a liquid jet; an evacuation lumen comprising a jet-receiving opening locatable opposite the nozzle to receive at least a portion of the liquid jet emitted from the nozzle, when the instrument is in operation, and which is configured and positioned to convey a flow of liquid away from the jet-receiving opening; and a nozzle alignment component located at or near, the distal end of the instrument that is configured and positioned to connect to the pressure lumen and, upon connection to the pressure lumen, to align the nozzle with respect to the evacuation lumen so that the liquid jet enters the jet-receiving opening along a selected trajectory, when the instrument is in operation are disclosed.

In another aspect, the invention is directed to nozzle assemblies of liquid jet-forming surgical instruments. In one series of embodiments, nozzle assemblies of liquid jet-forming surgical instruments comprising a nozzle providing component that is shaped to form a liquid jet; and a holder that is configured to retain and position the nozzle-providing component within the nozzle assembly, wherein the nozzle-providing component comprises a liquid flow passage having a diameter that continuously decreases along at least a portion of a liquid flow path through the liquid flow passage are disclosed.

In another series of embodiments, nozzle assemblies of liquid jet-forming surgical instruments comprising a nozzle-providing component that is shaped to form a liquid jet; and a holder that is configured to retain and position the nozzle-providing component within the nozzle assembly, wherein the holder comprises a recessed well having a seating surface comprising a hole, which hole is connectable in fluid communication with a source of pressurized liquid, the hole having an inner diameter less than an outer diameter of the nozzle-providing component when the nozzle-providing component is contained within the recessed well of the holder, and wherein the recessed well of the holder has an inner diameter at least as great as the outer diameter of the nozzle-providing component when the nozzle-providing component is contained within the recessed well of the holder are disclosed.

In another series of embodiments, nozzle assemblies of liquid jet-forming surgical instruments comprising a nozzle that is shaped to form a liquid jet; wherein the nozzle comprises a hole, defining a liquid flow path through the nozzle, which has surfaces that are optically smooth are disclosed.

In another series of embodiments, nozzle assemblies of liquid jet-forming surgical instruments comprising a nozzle that is shaped to form a liquid jet; wherein a ratio of a liquid flow path length through the nozzle to a minimum inner diameter of a jet-forming orifice of the nozzle does not exceed 4; and wherein the liquid jet formed by the nozzle assembly when in operation has a cone angle not exceeding 10 degrees are disclosed.

In another aspect, the invention is directed to methods for fabricating a nozzle assembly of a liquid jet-forming surgical instrument. In one series of embodiments, methods for fabricating a nozzle assembly of a liquid jet-forming surgical instrument comprising affixing a nozzle-providing component in the shape of a ring, the nozzle-providing component having an outer diameter and a liquid flow passage through the nozzle-providing component wherein the flow passage has a diameter that continuously decreases along at least a portion of a liquid flow path through the liquid flow passage, to or within a holder, the holder being connectable in fluid communication with a source of pressurized liquid, thereby forming the nozzle assembly, such that the nozzle assembly is able to withstand an internal liquid pressure of at least about 1,000 psig without failure are disclosed.

In another series of embodiments, methods assembling at least a portion of a liquid jet-forming surgical instrument, comprising connecting at least a distal portion of a pressure lumen, the pressure lumen comprising at or near its distal end a nozzle that is shaped to form a liquid jet, and at least a distal portion of an evacuation lumen, the evacuation lumen comprising a jet-receiving opening locatable opposite the nozzle, to a nozzle alignment component located at or near the distal end of the instrument, such that upon connection of the pressure lumen and the evacuation lumen to the nozzle alignment component without further alignment steps, the nozzle is aligned with respect to the evacuation lumen so that a liquid jet formed by the nozzle enters the jet-receiving opening along a selected trajectory, when the instrument is in operation are disclosed.

In another aspect, the present invention is directed to a method of making one or more of the embodiments described herein, for example, a liquid jet surgical instrument or a nozzle or a nozzle assembly of a surgical instrument. In yet another aspect, the present invention is directed to a method of using one or more of the embodiments described herein, for example, a liquid jet surgical instrument or a nozzle or a nozzle assembly of a surgical instrument. In still another aspect, the present invention is directed to a method of promoting one or more of the embodiments described herein, for example, a liquid jet surgical instrument or a nozzle or a nozzle assembly of a surgical instrument.

BRIEF DESCRIPTION OF THE DRAWINGS

The accompanying drawings are schematic are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In the drawings:

FIG. 4A is a perspective view of a liquid jet-forming surgical handpiece instrument including the nozzle assembly illustrated in FIG. 3B and a nozzle alignment component according to one embodiment of the invention;

FIG. 4B is a perspective view of a portion of the high pressure liquid supply and evacuation plumbing contained inside the body of the surgical instrument of FIG. 4A;

FIG. 5A is a cross-sectional side view of an alternative embodiment of a nozzle alignment component;

FIG. 5B is a cross-sectional view of the nozzle alignment component of FIG. 5A, taken along line 5B-5B;

FIG. 5C is a cross-sectional side view of a distal portion of a pressure lumen configured to mate with the nozzle alignment component of FIG. 5A, illustrating a holder as illustrated in FIG. 2A at it distal tip prior to insertion of a nozzle ring and fabrication of a complete nozzle assembly;

FIG. 5D is an enlarged cross-sectional detail view of the area encircled by arrows 5D-5D of the distal tip of the pressure lumen of FIG. 5C after insertion of the nozzle ring of FIG. 1E into the holder and formation of a nozzle assembly as illustrated in FIG. 3B;

FIG. 6A is a cross-sectional side view of another alternative embodiment of a nozzle alignment component including a nozzle assembly therein as illustrated in FIG. 3C;

FIG. 6B is a cross-sectional view of the nozzle alignment component of FIG. 6A, taken along line 6B-6B;

FIG. 6C is a cross-sectional view of the nozzle alignment component of FIG. 6A, taken along line 6C-6C;

FIG. 6D is a cross-sectional view of the nozzle alignment component of FIG. 6A, taken along line 6D-6D.

DETAILED DESCRIPTION

Figure 1A:
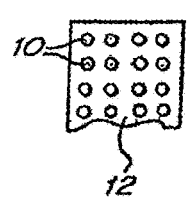
FIG. 1A is a plan view of a portion of a template for making a photomask as a step in a photolithographic electrodeposition method for fabricating nozzle rings according to an embodiment of the invention.

Disclosed are nozzles and nozzle assemblies of liquid jet-forming surgical instruments, surgical instruments employing such nozzles and/or nozzle assemblies, and methods of fabricating the nozzle assemblies in forming surgical instruments. Also, disclosed are liquid jet-forming surgical instruments including both liquid jet-forming nozzles and optional evacuation lumens, which when provided can be configured to receive the liquid jet and evacuate the liquid forming the liquid jet. Certain embodiments of such surgical instruments include inventive nozzle alignment component(s) to facilitate alignment of the nozzles and evacuation lumen upon assembly.

The surgical instruments provided according to certain embodiments of the invention and/or utilizing certain embodiments of the nozzles and/or nozzle assemblies of the invention, can take on many configurations, depending on the particular application. For example, as described in further detail in the context of FIGS. 4A-4C, the surgical instruments can comprise a surgical handpiece with a body designed to be gripped by the hand of an operator during a surgical or medical procedure. Alternatively, the surgical instruments can comprise an elongated tubular device, such as a catheter, or can take on other configurations. Additional configurations which can employ certain aspects of the present invention are discussed in Applicant's U.S. Pat. Nos. 5,944,686; 6,375,635 and 6,511,493, and commonly-owned U.S. Patent Publication 2003/0125660 A1. Such instruments typically include a "distal end" and a "proximal end." A "distal end" of surgical instrument, according to the invention, refers to that portion of the instrument that is adapted to perform a surgical procedure on a patient. The distal end typically includes such structure as the nozzle and nozzle assembly, a jet-receiving opening of an evacuation lumen, when an evacuation lumen is provided, a nozzle alignment component for certain embodiments, and, optionally, other tissue-contacting and/or tissue-altering components. While the "distal end" is typically located at a position on the instrument farthest from the operator during use (i.e., a distal-most position), this need not always be the case. The "proximal end" of the instrument refers to that portion of the instrument adapted to be controllable by an operator of the instrument. For embodiments wherein the instrument comprises a surgical handpiece, the proximal end typically includes a body configured and adapted to be grasped by the hand of an operator during use. While, in the discussion below, the surgical instruments are typically referred to as being "liquid jet" instruments, it should be understood that, while, in certain embodiments involving tissue cutting, the use of liquids to form the jet is preferred, in alternative embodiments, surgical instruments according to the invention could utilize fluids other than liquids, such as certain gases. Accordingly, whenever "liquid" or "liquid-jet" is indicated, the terms "fluid" (encompassing both liquids and gases) and "fluid jet," respectively, should be considered interchangeable, unless otherwise specified.

The invention also provides, in certain embodiments, kits including an inventive surgical instrument, or component thereof in combination with instructions directing an operator to dispose of at least the portion, and in some instances of the entire instruments, after a single use. "Instructions" can and often do define a component of promotion, and typically involve written instructions on or associated with packaging of instruments or components of the invention. Instructions also can include any oral or electronic instructions provided in any manner. The "kit" typically, and preferably, defines a package including both any one or a combination of the components and/or instruments of the invention and the instructions, but can also include the components and/or instruments of the invention and instructions of any form that are provided in connection with the components and/or instruments in a manner such that a clinical professional will clearly recognize that the instructions are to be associated with the specific components and/or instruments.

In one aspect, the invention provides a series of nozzles and/or nozzle assemblies for liquid jet-forming surgical instruments, as well liquid jet-forming surgical instruments employing such nozzles and/or nozzle assemblies. As described in greater detail below, certain embodiments of the inventive nozzles and nozzle assemblies can provide improved performance over conventional nozzles in that the nozzles and/or nozzle assemblies can improve one or more of the following performance characteristics: the degree of collimation of liquid jets formed by the nozzle, the ease and economy of manufacturing the nozzles and/or nozzle assemblies reproducibility and/or ease of fabrication and/or alignment of the nozzles along a desired, the ability to form relatively collimated liquid jets over relatively long jet lengths with lower pressure drops through the nozzle than in conventional nozzle designs, etc. Various embodiments of the nozzle assemblies, nozzles, and surgical instruments described below can achieve one or more of the above-described advantageous performance characteristics and, in certain embodiments, all of the above-described performance characteristics.

In certain embodiments, surgical instruments are provided that include a nozzle that is shaped to form a liquid jet, which has surfaces that are optically smooth. The term "optically smooth" as used herein refers to a surface that is smooth on the scale of the wavelength of visible light. As discussed further below, the ability to provide nozzles having such smooth surfaces can reduce the degree of induced turbulence in the liquid forming the jet, thereby improving the degree of collimation of the jet and reducing pressure drop across the nozzle during formation of the jet. As discussed in more detail below, one method of forming nozzles having optically smooth surfaces involves forming such surfaces using techniques involving the electrodeposition of conductive materials, such as metals.

The term "nozzle" as used herein refers to a lumen or conduit having a reduced inner diameter with respect to the inner diameter of a region of a conduit or container, with which the nozzle is in fluid communication, upstream of the nozzle. It should be noted that the reduced inner diameter of the nozzle may be constant, in certain embodiments, or may be stepped or tapered along the flow path through the nozzle. Moreover, the cross-sectional shape of the flow path through the nozzle can be any suitable shape. In certain embodiments, illustrated herein, the cross sectional shape is a circle. A "jet-forming orifice" or "jet opening" of a nozzle, as used herein refers to the smallest diameter orifice in the nozzle from which a liquid jet formed by the nozzle is emitted. The initial diameter of the liquid jet typically corresponds to the cross sectional diameter of the jet-forming orifice/jet opening. In certain embodiments, the invention provides a surgical instrument including a nozzle having a configuration enabling the nozzle to form a liquid jet that has the ability to remain collimated over longer distances than is typically achievable with conventional nozzles having the same ratio of liquid flow path length through the nozzle to minimum inner diameter of the jet forming orifice of the nozzle. In certain embodiments, discussed in more detail below, such inventive nozzles have the ability to form liquid jets characterized by a cone angle that is less than would be the cone angle formed by a typical nozzle of conventional design for a surgical liquid jet instrument and having the same ratio of liquid flow path length to minimum inner diameter of the jet forming orifice. A "liquid flow path length" through the nozzle or, equivalently, "nozzle length" as used herein refers to the length of the nozzle (see above definition of nozzle) as measured along a central axis of the hole comprising the flow path of the nozzle. A "cone angle" of a liquid jet is given its ordinary meaning and is illustrated and discussed in more detail in the context of FIG. 4C (where the cone angle of liquid jet 130 equals 2×A as illustrated).

In certain embodiments of the invention nozzle assemblies comprising nozzle-providing components and surgical instruments employing such nozzle assemblies are provided. A "nozzle assembly" as used herein refers to an operative assembly of at least two sub-components, which together provide a nozzle that is shaped to form a liquid jet. In certain embodiments, the at least two sub-components may comprise the above-mentioned nozzle-providing component and a holder that is configured to retain and position a nozzle-providing component in the nozzle assembly. A "nozzle assembly" as used herein would not apply to a nozzle structure that is integrally formed in a container or lumen, such as a hole in a wall of such container/lumen or a necked-down region of an outlet end of such a lumen. A "nozzle-providing component" as used herein refers to a sub-component of a nozzle assembly that includes as part of its structure a nozzle.

As discussed and illustrated in more detail below, in certain embodiments of the invention, in order to improve the efficiency of the inventive nozzles and nozzle-providing components and provide a vena contracta effect, the nozzle-providing component can comprise a liquid flow passage having a diameter that continuously decreases along at least a portion of its length, and in certain embodiments continuously decreases along essentially the entirety of its length. As discussed and illustrated in more detail below, in one series of embodiments, such a liquid flow passage through the nozzle-providing component is provided by fabricating the nozzle-providing component so that it has a curved cross-sectional profile, and in one embodiment a semicircular profile. The provision of a liquid flow path through the nozzle-providing component having a continuously decreasing diameter along the direction of liquid flow, according to certain embodiments of the invention—especially for those embodiments wherein the cross-sectional shape of the nozzle-providing component is semicircular and/or the surfaces of the liquid flow path are optically smooth—can enable the inventive nozzle-providing components to produce liquid jets having a desirable degree of collimation while also having a liquid flow path that is relatively short, which can lead to a reduced pressure drop for the nozzle compared with many conventional surgical liquid jet instrument nozzle designs. For example, in certain embodiments, the nozzle-providing component comprises a ring that has an outer diameter not greater than 0.1 inch and height, as measured in a direction parallel to the longitudinal axis of the hole defining the liquid flow path through the ring, that is less than the outer diameter of the ring. A "ring" as used in the above-context in describing certain nozzle-providing components of the invention refers to such a component having the shape of a torus, wherein the cross-sectional shape of the torus, taken in a plain containing the central axis of the hole of the torus, can be any closed plane curve, e.g. a circle, rectangle, triangle, semicircle, etc. As mentioned above, in one particular embodiment, which is illustrated in FIG. 1E, the cross-sectional shape of the ring is a semicircle.

In another aspect, the invention also provides surgical instruments. The surgical instruments include a pressure lumen that is configured and positioned to convey a flow of liquid to a nozzle shaped to form a liquid jet positioned at or near the distal end of the pressure lumen. Certain surgical instruments also include an optional evacuation lumen comprising a jet-receiving opening locatable opposite the nozzle to receive at least the portion of the liquid jet that is emitted from the nozzle, when the instrument is in operation, and which is configured and positioned within the instrument to convey a flow of liquid away from the jet-receiving opening toward the proximal end of the instrument. Certain embodiments of such surgical instruments include an inventive nozzle alignment component located at or near the distal end of the instrument that is configured and positioned, as described in more detail below in the context of FIGS. 4A-6D, to connect to the pressure lumen and, upon connection to the pressure lumen, to align the nozzle with respect to the evacuation lumen so that the jet enters the jet-receiving opening along a selected trajectory, when the instrument is in operation. In certain embodiments (e.g. see FIGS. 4A-5D), the nozzle alignment component is configured to connect to both the pressure lumen and the evacuation lumen to provide the above-described alignment. In an exemplary embodiment, for example, as illustrated in FIGS. 4A-5D, the nozzle alignment component comprises an insert including a groove and/or a lumen therein that is sized and configured to contain and secure the distal end of the pressure lumen. In certain such embodiments, a downstream end of the insert may also be sized and configured to be insertable in the jet-receiving opening of the evacuation lumen.

The invention also provides methods of fabricating the above-described surgical instruments and nozzle assemblies. In one such method of fabrication of a nozzle assembly according to the invention, described in more detail below, the nozzle assembly is fabricated by combining a nozzle-providing component, such as a nozzle ring, with a holder that secures and positions the nozzle-providing component and is connectable to a source of pressurized fluid. In a first step of an embodiment of such a method, a nozzle ring is fabricated by a technique that is preferably able to produce desirable quantities of such nozzle rings economically and reproducibly. Any suitable technique may potentially be used to fabricate nozzle rings that will provide a desirable level of reproducibility, uniformity, smoothness, and fabrication economy. In one preferred embodiment, the nozzle rings are obtained that are made by a photolithographic technique coupled with subsequent electrodeposition, as described in more detail below in the context of FIGS. 1A-1E. Nozzle rings fabricated according to this technique can be stable, and can typically be readily handled manually or by machine and subject to quality control inspection, etc., before being assembled into a nozzle assembly of a surgical instrument. In alternative embodiments, nozzle-providing components or nozzle rings could also be made by other techniques, such as by drilling of preform blanks e.g. via mechanical drilling, laser drilling, electric discharge machining, or any other known technique capable of reliably forming holes with a desired jet-forming orifice diameter (e.g. with in the range of about 0.001 to 0.02 inch). In one embodiment, a laser can be used to cut both the central hole defining the nozzle in a nozzle ring and an outer circle in a larger blank defining the outer diameter of the nozzle ring. In another embodiment, nozzle rings are fabricated by slicing a piece of tubing having suitable inner and outer diameters.

A subsequent step of the exemplary fabrication method can involve forming or providing a nozzle-providing component holder, into which the nozzle-providing component is installed, and to which a source of high-pressure liquid is in fluid communication or can be connected in fluid communication. A variety of configurations and materials can be utilized in forming the holder of the nozzle assembly. In certain embodiments, a structure in which the holder is formed comprises high pressure tubing forming a pressure lumen of the surgical instrument. Such tubing can be selected to be suitable for connection to a source of liquid having a pressure desirable for operation of the instrument, e.g. in excess of 1,000 psig, 3,000 psig, 5,000 psig, 10,000 psig, 15,000 psig, 30,000 psig, 50,000 psig, or more. The tubing also, desirably, is configured to facilitate bending as required to form desired configurations of the distal portion of the pressure lumen of the surgical instrument (e.g. see FIGS. 4A-6D and associated discussion).

In certain embodiments, the holder is formed, for example in thin-walled tubing comprising the pressure lumen, by creating a recessed well in the tubing or other holder structure, wherein the recessed well has a seating surface having a bore therethrough that is in fluid communication with the pressure lumen of the instrument. In order to retain and position the nozzle ring or other nozzle-providing component, the inner diameter of the bore through the seating surface should be less than the outer diameter of the nozzle-providing component. As described in more detail below, depending on the technique utilized for 1.5 affixing the nozzle-providing component within the recessed well, the inner diameter of the recessed well may be at least as great as the outer diameter of the nozzle-providing component, when it is in a relaxed configuration prior to insertion in the recessed well, or, in other embodiments, may be somewhat smaller in diameter, so that the nozzle-providing component can be press fit and somewhat deformed upon insertion in to the recessed well.

Figure 2A:
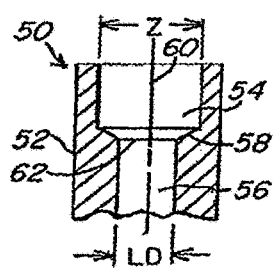
FIG. 2A is a cross-sectional side view of a nozzle-providing component holder of a nozzle assembly, according to one embodiment of the invention.
Figure 2B:
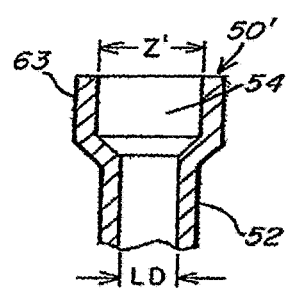
FIG. 2B is a cross-sectional side view of a nozzle-providing component holder of a nozzle assembly, according to another embodiment of the invention.

In certain preferred embodiments, the shape and size of the recessed well is selected such that, upon insertion of the nozzle-providing component into the well, the nozzle-providing component becomes automatically positioned, via mating interaction with contacting surfaces of the recessed well of the holder, such that a liquid jet formed by the nozzle of the nozzle-providing component will be directed along a desired trajectory within the surgical instrument. In certain embodiments, the recessed well is formed in tubing comprising the pressure lumen at a distal tip of the pressure lumen. A "distal tip" of the pressure lumen as used herein refers to the distal-most end and outlet of the pressure lumen, e.g. as illustrated in FIGS. 2A and 2B. As discussed above, the recessed well typically comprises a region of the tubing or holder structure having an inner diameter that is larger than the inner diameter of the bore through the seating surface. This enlarged inner diameter section may be made by any suitable technique, for example, by drilling, boring, flaring, etc. In certain embodiments, the enlarged inner diameter section is made by localized stretching and expansion of the distal tip of the pressure lumen, e.g. as illustrated and discussed in the context of FIG. 2B. In alternative embodiments, a nozzle ring or other nozzle-providing components may, instead of being installed into a well formed directly in the distal tip or side wall of the pressure lumen, be installed in a plate or other structure, in which a holder of similar configuration to that described above is formed. In certain preferred embodiments, the inner diameter of the hole formed in the seating surface of the holder is substantially larger than the smallest diameter of the jet opening of the nozzle of the nozzle-providing component, for example, in certain embodiments it is at least twice as great in diameter, and in other embodiments it is at least three or four, or more, times larger.

The nozzle-providing component, such as a nozzle ring, can be affixed and secured to or within the holder, such that the nozzle assembly thus formed is able to withstand an internal liquid pressure at least as great as that expected to be utilized for forming the liquid jet of the surgical instrument, for example at least about, without failure of the nozzle assembly, e.g., by mechanical failure or undesirable leakage or misdirection of liquid. As described in greater detail below, a variety of ways of affixing and securing the nozzle-providing component within the nozzle assembly may be utilized. In certain embodiments, the nozzle-providing component is secured alter its insertion into a recessed well positioned at a distal tip of high pressure tubing by crimping the end of the tubing, so that the nozzle-providing component is prevented from moving. In other embodiments, separate structures may be utilized for retaining and securing the nozzle-providing component, such as retaining rings, caps, plates, etc. Other means of retention within the scope of the invention can include, without limitations, the use of adhesive, welding, brazing, soldering, or any other suitable means of retention, know to those skilled in the art.

In certain embodiments, wherein the seating surface of the holder is positioned downstream of the nozzle-providing component, because the fluid pressure exerted on the nozzle-providing component forming the liquid jet tends to force the nozzle-providing component against the seating surface, the securing means utilized to hold the nozzle-providing component in place need not be able to provide a high level of retention force, and can include securing components such as elastomer O-rings, adhesives, deformable lightweight metal or plastic retainers (e.g. locking washers, etc), disks or rings of paper or other fibrous materials, screens, etc. Such restraints need only prevent the nozzle-providing component from becoming incorrectly positioned in the absence of water pressure. In certain such embodiments, a disk or plug of filter paper or other material permeable to liquid flow, and lacking any central hole, is used both to retain the nozzle-providing component and to prevent its plugging by debris (see, e.g. FIG. 6A).

Fabrication of exemplary nozzle assemblies, according to the invention, including a specific embodiment of a nozzle-providing component in the form of a nozzle ring is described below in the context of FIGS. 1A-3C. One exemplary embodiment for fabricating a nozzle ring and a nozzle ring formed thereby is illustrated in FIGS. 1A-1-E. Rings produced by the illustrated method or similar methods and having the characteristics, dimensions and configurations described and illustrated in FIGS. 1A-1E are available for fabrication commercially and were obtained from Dynamics Research Corporation (Wilmington, Mass.). The illustrated method comprises a photolithographic technique, wherein the nozzle rings are formed via the electrodeposition of a metal. The exemplary nozzle ring forming method described below is similar in certain respects to that disclosed in U.S. Pat. No. 4,954,225, which is incorporated herein by reference.

Figure 1B:
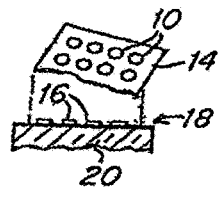
FIG. 1B is a schematic illustration of a portion of a photomask and a portion of a substrate having conductive features thereon, for forming nozzle rings by electrodeposition as a step in a photolithographic electrodeposition method for fabricating nozzle rings according to an embodiment of the invention.
Figure 1C:
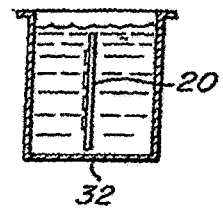
FIG. 1C shows, schematically, an electrodeposition step of a photolithographic electrodeposition method for fabricating nozzle rings according to an embodiment of the invention.

Referring to FIGS. 1A-1C, an array of circles 10 is first printed on a substrate 12, and the printed array can be converted to a photolithography mask 14 by conventional techniques. As illustrated in FIG. 1B, mask 14 is used, to produce a congruent array of conductive circles 16 in a thin layer of a photoresist material 18 on a glass plate 20. While, in the presently illustrated embodiment, the photolithography mask 14 includes feature forming elements 10 having the shape of a circle, in other embodiments other shapes may be utilized. As explained below, the shape of elements 10 dictates the perimetric shape of the nozzle ring, which is selected to correspond to the cross-sectional shape of the holder in which the nozzle ring will be placed. In the illustrated embodiment, the holder of the nozzle assembly, such as a distal tip of the pressure lumen, has a circular cross-section, so that the nozzle rings are formed having a perimetric shape that is circular, as illustrated in FIG. 1F. In addition, as explained in more detail below, the diameter of elements 10 corresponds to a diameter of a center line 22 of the solid portion of the ring, thereby also affecting the outer diameter OD of the ring 21 and the inner diameter ND of the hole 28 in the ring defining the jet opening of nozzle 30 (see FIG. 1E). As explained in more detail below, these values are selected based upon the desired initial diameter of the liquid jet (for inner diameter ND) and the inner diameter of the recessed well portion of the holder (for outer diameter OD of ring 21). Referring again to FIG. 1B, when the rings are duplicated on an appropriate scale in a photoresist material and it is developed, small, thin circular lines 16 of conductive material are produced on glass plate 20.

Figure 1D:
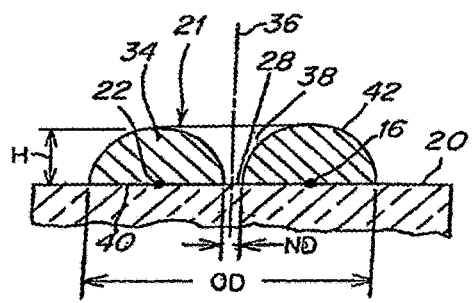
FIG. 1D is a cross-sectional side view of a nozzle ring formed by a photolithographic electrodeposition method for fabricating nozzle rings according to an embodiment of the invention, still attached to the substrate on which it was formed.
Figure 1E:
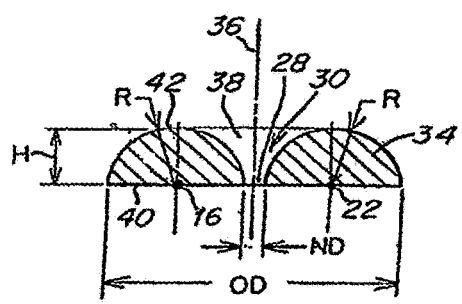
FIG. 1E is a cross-sectional side view of the nozzle ring of FIG. 1D, after separation from the substrate.

While a variety of known electroplating/electrodeposition techniques can potentially be utilized for forming the nozzle rings 21, in the illustrated embodiment, referring to FIG. 1C, plate 20 bearing the conductive circles 16 is placed in a plating bath 32. In the illustrated embodiment, metal, for example a nickel-cobalt alloy is plated and allowed to build up uniformly on the conductive regions 16, producing a ring 21 in the shape of a ring torus, wherein the ring torus is hemispherical, such that a cross-section 34 of the ring by a plane containing the longitudinal axis 36 of the hole 38 defining the liquid flow path through the ring, has the shape of a semicircle, as illustrated in FIGS. 1D and 1E. After a selected time in plating bath 32, nozzle ring 21 attains a desired thickness H so as to produce a central hole 38 comprising a nozzle 30 with a desired minimum ND comprising a jet opening 28 of nozzle 30. Nozzle ring 21, as illustrated in FIG. 1D, has the above-described hemispherical shape analogous to a ring torus having a circular cross-section (i.e. like a bagel) which has been sliced in half through a central plan perpendicular to axis 36 of its hole 38 (e.g. like slicing a bagel along its "equator" to make a bagel sandwich). As discussed below, the minimum diameter portion of hole 38, which is on flat surface 40 of nozzle ring 21, is, in certain preferred embodiments, used as the jet opening 28 of nozzle 30 in that it is used as the exit for fluid passing through nozzle ring 21, when it is oriented in a functioning nozzle assembly.

The utilization of electrodeposition of metal in the above-described exemplary embodiment for forming the nozzle ring is one way to enable the curved surfaces 42 of nozzle ring 21 to be extremely smooth, for example to be optically smooth as defined previously. As indicated in FIG. 1E, semicircular cross-section 34 is characterized by a radius R having as its origin conductive circle 16 initially formed in the step illustrated FIG. 1B. Radius R also, in the illustrated embodiment, defines the height H of nozzle ring 21 and the length of nozzle 30.

Finished nozzle rings 21 can be detached from plate 20, by conventional means, and, if required, cleaned in preparation for inserting them into holders for forming the inventive nozzle assemblies, as described in further detail in FIGS. 2A-3C. A detached nozzle ring 21 is illustrated in cross-section in FIG. 1E. Referring to FIG. 1E, a variety of exemplary dimensions are given below, which have been found useful in the practice of certain exemplary embodiments of the invention and for constructing certain exemplary embodiments of the surgical instruments described below and illustrated in FIGS. 4A-6D. It should be emphasized that the particular dimensions selected will depend on the desired performance of the nozzle ring and the dimensions of various other components, for example the inner and outer diameter of the pressure lumen of a surgical instrument of the invention, etc. and must be selected based on such considerations.

In particular embodiments, nozzle ring 21 will have an outer diameter OD not greater than about 0.1 inch and a height H that is less than the outer diameter. In certain such embodiments, the outer diameter OD of nozzle ring 21 is between 0.02 inch and 0.1 inch. In certain other embodiments, outer diameter OD of nozzle ring 21 is between 0.03 inch and 0.04 inch and the height H of the ring is between 0.005 inch and 0.01 inch. In one exemplary embodiment, where the nozzle ring is used for forming a nozzle assembly in a distal tip of a pressure lumen, which pressure lumen has an inner diameter of 0.03 inch and an outer diameter of 0.05 inch, the outer diameter OD of ring 21 is about 0.034 inch and the height H of the ring is about 0.007 inch. In certain exemplary embodiments, the minimum diameter ND of jet opening 28, which defines the initial diameter of the liquid jet emitted from nozzle ring 21 in operation, is between about 0.001 and about 0.02 inch, in certain embodiments is between about 0.002 inch and about 0.01 inch, and in certain embodiments is between about 0.003 and about 0.007 inch. In one exemplary embodiment, inner diameter ND is about 0.005 inch.

As mentioned above and as described in further detail below, because nozzle ring 21 can have extremely smooth liquid contacting surfaces 42 on the upstream side of the nozzle ring and a gradually decreasing inner diameter of nozzle 30, the nozzle ring can have the ability to form highly collimated liquid jets even for relatively low ratios of nozzle length H to jet opening diameter ND. For example, it has been found in the context of the present invention that a liquid jet formed by a nozzle ring, such as nozzle ring 21 can have a cone angle not exceeding 10 degrees, when the ratio of nozzle length H to jet opening diameter ND does not exceed 4, in certain embodiments when the ratio does not exceed 2, and in certain other embodiments where the ratio does not exceed 1.5. In certain such embodiments, the liquid jet formed can have a cone angle between 3 degrees and 6 degrees. The cone angle refers to the angle formed at the apex of the liquid jet (see FIG. 4C, wherein the cone angle equals 2×A).

Figure 2C:
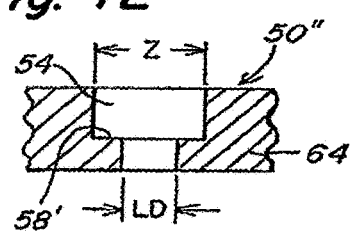
FIG. 2C is a cross-sectional side view of a nozzle-providing component holder of a nozzle assembly, according to another embodiment of the invention.

FIGS. 2A-2C illustrate three exemplary configurations of nozzle-providing component holders of inventive nozzle assemblies provided by the invention. Referring to FIG. 2A, holder 50 comprises a distal tip of tubing 52, which may be a pressure lumen of a surgical instrument of the invention, which has been bored to produce a recessed well 54 having an inner diameter Z greater than the inner diameter LD of lumen 56 of the tubing 52. The base of recessed well 54 comprises a seating surface 58, which, as explained in further detail below, serves to position and orient a nozzle ring or other nozzle-providing component inserted into the holder. Seating surface 58 may, optionally, be beveled, as illustrated, to assist in retention and orientation of a nozzle ring, as explained in more detail below.

Figure 3A:
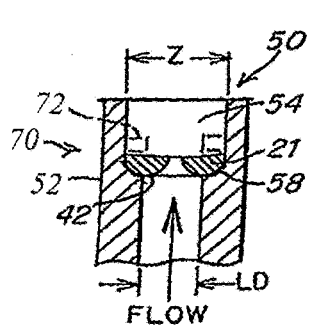
FIG. 3A is a cross-sectional side view of a nozzle assembly including the nozzle ring of FIG. 1E and the holder of FIG. 2A, according to one embodiment of the invention.
Figure 3B:
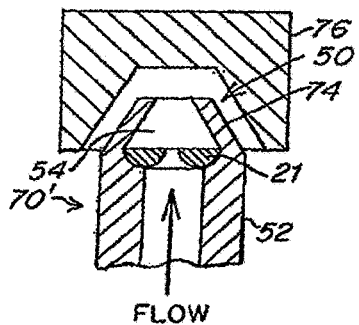
FIG. 3B is a cross-sectional side view of a nozzle assembly including the nozzle ring of FIG. 1E and the holder of FIG. 2A, according to another embodiment of the invention.
Figure 3C:
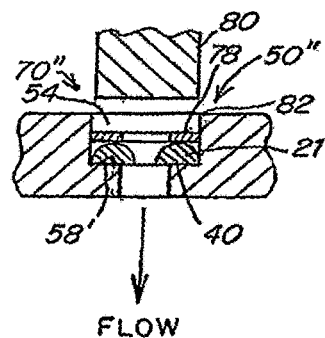
FIG. 3C is a cross-sectional side view of a nozzle assembly including the nozzle ring of FIG. 1E and the holder of FIG. 2C, according another embodiment of the invention.

As explained in more detail below in the context of FIGS. 3A-3C, the selection of the inner diameter Z of recessed well 54, in comparison with the outer diameter OD of nozzle ring 21, will depend upon the technique utilized for securing the nozzle ring within the holder. For embodiments, such as illustrated in FIG. 3A below, wherein seating surface 58 is located upstream of the nozzle ring, such that pressure applied to the ring, as liquid passes through the nozzle ring in forming the liquid jet, tends to force the nozzle ring away from the seating surface so that the nozzle ring must be strongly retained in recessed well 54 to resist such pressure and force, and wherein the retaining force is provided via press fitting an oversized nozzle ring into recessed well 54, the recessed well of the holder should have an inner diameter Z somewhat less than the outer diameter OD of the nozzle ring as measured when the nozzle ring is in an unstressed configuration prior to insertion of the nozzle ring into the recessed well of the holder. In other embodiments, such as illustrated in FIG. 3B or 3C, wherein a retaining means positioned downstream of the nozzle ring (FIG. 3B) or upstream of the nozzle ring (FIG. 3C) is provided, inner diameter Z of recessed well 54 can be equal to or somewhat larger than outer diameter OD of the nozzle ring 21. For example, for an exemplary embodiment of such a configuration where outer diameter OD of nozzle ring 21 is about 0.034 inch, inner diameter Z of recessed well 54 can be selected to be between about 0.035 and about 0.04 inch. Typically, in the above-described embodiments wherein Z is somewhat larger than OD, the degree of oversize can range between about 1% and about 20%, in certain embodiments between about 5% and about 15%.

Holder 50, as illustrated, is configured to retain and position a nozzle-providing component in a configuration in which a liquid jet formed by a nozzle of the nozzle-providing component is directed along a desired trajectory. For example, referring to FIG. 2A, if it is desirable that a liquid jet formed by the nozzle-providing component, when assembled into a nozzle assembly comprising holder 50, is oriented co-linear with longitudinal axis 60 of pressure lumen 56, then seating surface 58 should provide a seat co-planar to or geometrically centered about a plane perpendicular to longitudinal axis 60, as is illustrated in FIG. 2A.

The inner diameter LD of hole 62 through seating surface 58 is selected, in certain embodiments, to be less than the outer diameter OD of nozzle ring 21. For example, in an exemplary embodiment where OD of nozzle ring 21 is about 0.034 inch, LD of hole 62 may be in the range of between about 0.02 and about 0.03 inch. The specific dimension selected for LD is, typically, not critical. In certain embodiments, however, it is preferred that LD be greater than the inner diameter ND of jet opening 28 of nozzle ring 21 by at least a factor of about 2, and certain embodiments by at least a factor of about 4, and certain embodiments by at least a factor of about 6. Conveniently, LD can be selected to be equal to the inner diameter of lumen 56 of tubing 52 comprising holder 50.

FIG. 2B illustrates an alternative embodiment illustrating a holder 50', which is substantially similar to holder 50 illustrated in FIG. 2A, except that recessed well 54 is formed in tubing 52 by expanding a distal tip 63 of tubing 52 to form the recessed well 54 having expanded the inner diameter Z'.

FIG. 2C illustrates yet another embodiment for providing a holder 50" of a nozzle assembly of the invention, wherein the holder comprises a recessed well 54 formed in a plate or side wall of a pressure container, as opposed to at a distal end of a length of tubing, as previously illustrated. In one embodiment, wall 64 of holder 50" comprises a side wall of high pressure tubing forming a pressure lumen of a surgical instrument provided with a nozzle assembly of the invention. As illustrated, recessed well 54 of holder 50" includes a seating surface 58' that is essentially planar, instead of beveled, or slanted as previously illustrated. As illustrated and discussed below in the context of FIG. 3C, planar seating surfaces can be advantageous for use when the seating surface is positioned downstream of the nozzle-providing component in the nozzle assembly (as illustrated in FIG. 3C), wherein, when a nozzle ring such as illustrated in FIG. 1E is utilized, the flat surface 40 of the nozzle ring 21 can contact and make sealing contact with seating surface 58'.

FIGS. 3A-3C illustrate several exemplary embodiments for the affixing, securing, and retaining of a nozzle-providing component, such as nozzle ring 21 in a holder to construct an operable nozzle assembly provided according to the invention. Referring to FIG. 3A, nozzle assembly 70 comprises holder 50, previously illustrated in FIG. 2A, into which nozzle ring 21 has been inserted. Nozzle ring 21 has been inserted into recessed well 54 of holder 50 of nozzle assembly 70 so that its curved surfaces 42 face the high pressure of the upstream side of the fluid flow path through tubing 52. For nozzle-providing components including a flat side and a side having curvature providing a hole through the nozzle-providing component that is tapered, such as illustrated, it is preferred to orient such a nozzle-providing component so that the curved surfaces face upstream, thereby providing a nozzle having a decreasing inner diameter along the length of the fluid flow path through the nozzle, which can enhance the efficiency and vena contracts effect of the nozzle, as previously described.

In the exemplary embodiment illustrated in FIG. 3A, nozzle ring 21 has an outer diameter OD, as measured in a relaxed configuration, that is somewhat larger than the inner diameter Z of recessed well 54 of holder 50. In order to affix nozzle ring 21 within holder 50 in a pressure-stable fashion, nozzle ring 21 can be press-fit into recessed well 54. When such a method of inserting and securing nozzle ring 21 is utilized, nozzle assembly 70 need not include any additional retaining elements positioned in the holder downstream of the nozzle-providing component (i.e. need not include an optional nozzle retaining element 72 shown in dotted outline and discussed in more detail below). As mentioned previously, in order to ensure that nozzle assembly 70, including a nozzle ring 21 having an outer diameter OD when in an unstressed configuration that is somewhat larger than the inner diameter Z of recessed wall 54 of holder 50, is pressure stable at desired operating pressures, a selected degree of oversize of the outer diameter of nozzle ring 21 enabling the nozzle ring to withstand operating pressures without becoming dislodged from the holder is provided. In certain embodiments, it has been found that sufficient pressure stability of the nozzle assembly can be provided when the outer diameter OD of the unstressed nozzle ring exceeds the inner diameter ring Z of the recessed well of the holder by less than 10%, and in certain embodiments by an amount between about 1% and 3%. As illustrated in FIG. 3A, when an oversized nozzle ring is press-fit into recessed well 54 of a holder 50, the planar configuration of flat surface 40 of nozzle ring 21 will tend to become distorted into a curved or conical shape, so that pressure forces applied to the upstream side of nozzle ring 21 will have a tendency to attempt to flatten and expand the outer diameter of the nozzle ring, thereby increasing the retaining force supplied by the inner walls of the recessed well, thus improving sealing and retention of the nozzle ring.

As mentioned above in the context of FIGS. 2A and 2B, for certain embodiments in which a curved surface 42 of, a nozzle ring mates with a seating surface 58 of a holder, it may be advantageous, for providing increased surface area of contact between the ring and the seating surface, that the seating surface be slanted or beveled. Such a slanted or beveled seating surface can be formed via a variety of conventional machining techniques and can comprise, for example, a counter bore providing essentially flat angled surfaces, a counter sync bore, providing conical seating surfaces, or a ball seat, providing curved seating surfaces. In certain embodiments, it is preferred that the seating surface be beveled with a counter sync bore, thereby providing conical seating surfaces.

As mentioned above, it is desirable that the nozzle assemblies formed according to the invention be able to withstand desirable operating pressures for forming liquid jets without failure, undesirable leakage, or undesirable misorientation of a liquid jet due to displacement of the nozzle-providing component within the holder. For example, in certain embodiments, it is desirable for a nozzle-providing component to be secured and retained by the holder sufficiently such that the nozzle assembly is able to withstand an internal liquid pressure of at least about 1,000 psig without failure, in certain embodiments, at least about 2,000 psig without failure, in certain embodiments, at least about 3,000 psig without failure, in certain embodiments, at least about 5,000 psig without failure, in certain embodiments, at least about 10,000 psig without failure, in certain embodiments, at least about 15,000 psig without failure, in certain embodiments, at least about 30,000 psig without failure, and yet in other embodiments, at least about 50,000 psig or more without failure.

For added strength and stability, especially for embodiments in which the outer diameter OD of nozzle ring 21 is the same as or somewhat less than inner diameter Z of recessed well 54 of a holder of a nozzle assembly of the invention, an additional retaining element, such as retaining element 72, can be provided downstream of the nozzle ring 21 to retain and secure it within the nozzle assembly. Such a retaining element can be any suitable retaining means such as one of those previously mentioned. In certain embodiments, retaining element 72 can comprise a rigid ring or disk press-fit into the recessed well, or a weld or solder bead. In another embodiment, as illustrated in FIG. 3B, the retaining element can comprise a region 74 of tubing 52 at its distal tip and downstream of nozzle ring 21 that has been crimped, for example with a crimping die 76 to compress the tubing downstream of the ring so that the nozzle ring is securely contained within nozzle assembly 70'.

FIG. 3C illustrates an embodiment of a nozzle assembly 70" utilizing holder 50" illustrated and discussed above in the context of FIG. 2C. In nozzle assembly 70", seating surface 58' is located downstream of nozzle ring 21, such that pressurized liquid passing through the nozzle ring and forming the liquid jet tends to force flat surface 40 of the nozzle ring into contact with planar seating surface 58'. In the embodiment illustrated in FIG. 3C, a retaining element 78 is used to hold nozzle ring 21 in place in recessed well 54 of holder 50". Retaining element 78 may be inserted via press fitting with a swage 80 to provide sufficient retaining force to hold nozzle ring 21 in place. Alternatively, with or without retaining element 78, a swaging device such as swage 80 could be used to deform the upper edge 82 of recessed well 54 sufficiently to retain nozzle ring 21. Because, in operation, nozzle ring 21 is not subject to large forces tending to displace it within recessed well 54 of nozzle assembly 70", the retaining element need not be particularly rigid or robust and may comprise elements such as, for example, a porous screen, mesh, disk of filter paper, porous plug, etc. Such retaining elements can also, in certain embodiments, provide a desirable filtering function to prevent debris from lodging within a nozzle 30 of nozzle ring 21 during operation.

Figure 4C:
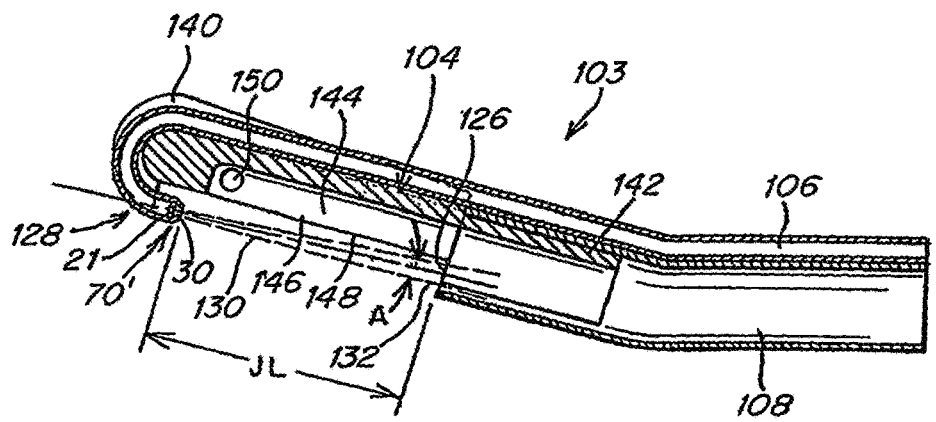
FIG. 4C is a cross-sectional view of the distal end of the surgical instrument of FIG. 4A taken along line 4C-4C.

FIGS. 4A-4E illustrate one exemplary embodiment of a surgical instrument provided according to the invention employing an inventive nozzle or nozzle assembly of the invention and/or an inventive nozzle alignment component of the invention. It must be emphasized that the exemplary embodiment illustrated is merely one of a large variety of instruments having a wide variety of configurations and utilizing liquid jets for a wide variety of purposes for which the inventive nozzle or nozzle assemblies and/or nozzle alignment components of the invention can be utilized. For example, while the liquid jet formed by instrument 100 illustrated in FIG. 4A is utilized for cutting and/or ablating and evacuating tissue 102 of a patient, in other embodiments, the liquid jet may be utilized for other purposes. For example, the liquid jet may, in certain embodiments, be utilized solely to drive evacuation and/or for driving rotation of a rotatable component of the instrument, such as a grinding burr or drill. In addition to surgical instrument 100 illustrated in FIGS. 4A-4E, the inventive nozzles or nozzle assemblies and/or nozzle alignment components described herein could be utilized for constructing other liquid jet-forming surgical instruments described, for example, commonly-owned U.S. Pat. Nos. 5,944,686; 6,375,635 and 6,511,493, and commonly-owned U.S. Patent Publication 2003/0125660 A1, incorporated by reference above.

Additionally, because many of die configurations, dimensions, materials, methods of fabrication, geometric and dimensional relationships between components, etc. of surgical liquid jet instrument 100 have been previously described in detail in, for example, commonly-owned U.S. Pat. Nos. 5,944,686; 6,375,635 and 6,511,493, and commonly-owned U.S. Patent Publication 2003/0125660 A1, such details are not repeated herein. The reader is referred to the above-mentioned US patents and patent publication for more details. In general, the various materials, configurations, dimensions, interrelationships, etc. recited in the above-mentioned commonly owned U.S. patents and patent publication are applicable in forming surgical liquid jet instruments, such as liquid jet instrument 100, according to the present invention, except as noted below. For example, surgical jet instruments according to the present invention, in certain embodiments, will include one or more of the above-described inventive nozzles or nozzle assemblies and/or the above- and below-described nozzle alignment components specifically set forth and described herein.

FIGS. 4A and 4B illustrate one embodiment of an assembled surgical handpiece instrument 100 having a distal end 103 including one embodiment of a nozzle alignment component 104 (illustrated in greater detail in FIGS. 4C-4E) provided according to the invention. Tissue to be treated with the surgical hand piece is denoted at 102. High pressure lumen 106 and evacuation lumen 108 enter handpiece body 110, which in the illustrated embodiment, comprises two mated sections 112 and 114. In certain embodiments, body 110 need not be pressure-tight (i.e., it need not sustain internal pressure). In such embodiments, body 110 can advantageously include slots or other openings connecting the inside of the body to the surrounding atmosphere to facilitate sterilization of the internal components within the body. Components 112 and 114 of hand piece body 110 can be connected together by any convenient means apparent to those of ordinary skill in the art such as including, but not limited to, screw connectors, tab-in-slot connections, adhesives, etc.

Two tubes emerge from the proximal end 116 of the hand piece body: a low pressure evacuation tube 118 and a flexible high pressure hose 120, each of which can be made of a variety of suitable materials as would be apparent to those of ordinary skill in the art. In one particular embodiment, each of the above-mentioned tubes is made of a suitable polymeric material. Connections within body 110 facilitating fluid communication between high pressure lumen 106 and flexible high pressure hose 120 and between evacuation lumen 108 and low pressure evacuation tube 118 are illustrated in FIG. 4B. While, in the illustrated embodiment high pressure connection 122 and low pressure connection 124 are located within handpiece body 110, in alternative embodiments, the connections can be made either proximally or distally of the handpiece body. In yet other embodiments, high pressure lumen 106 and/or evacuation lumen 108 may simply be provided having a length sufficient to extend completely through handpiece body 110 and, alternatively, proximally thereof, such that a separate high pressure line and suction tube need not be provided. High pressure connection 122 can comprise a wide variety of high pressure fittings rated to withstand applied operating pressures, which connections are well known to those skilled in the art and are described in greater detail in commonly-owned U.S. Pat. No. 6,375,635. Similarly, low pressure connector 124 can be any of a wide variety of suitable tubing connections well known to those of ordinary skill in the art and as described in the above-mentioned U.S. Pat. No. 6,375,635.

High pressure hose 120 is connected to a source of pressurized liquid (e.g., a high pressure pump—not shown). Evacuation tube 118 can be connected to a suitable container for containing and storing recovered fluid and debris, and, optionally, containing a filtered outlet for entrained air (not shown). In certain embodiments, the evacuation lumen 108 is shaped and positionable to enable it to remove from a surgical site at least a portion of tissue excised by the liquid jet formed by the nozzle during operation. In certain embodiments, the evacuation lumen is shaped and positionable to enable evacuation of essentially all of the liquid comprising the liquid jet from jet receiving opening 126 of the evacuation lumen 108 to the proximal end 116 of the instrument, without the need for an external source of suction. In other embodiments, wherein the surgical handpiece requires or utilizes a source of external suction to facilitate evacuation, evacuation tube 118 can be connected in fluid communication with a suitable source of suction, such as a vacuum pump, aspirator, house vacuum line, etc.

Figure 4D:
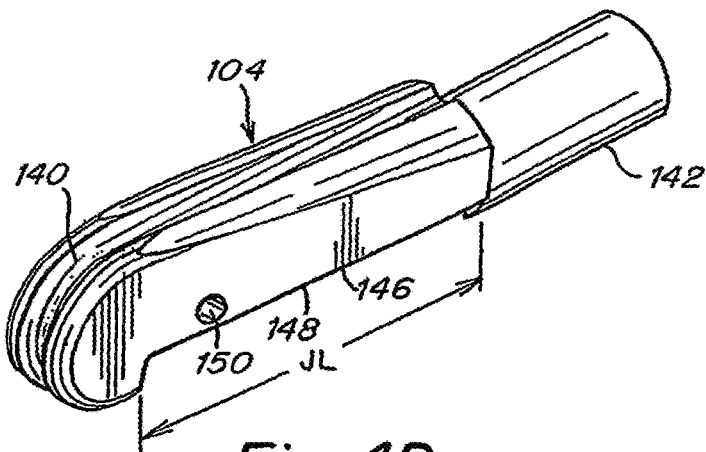
FIG. 4D is a perspective view of the nozzle alignment component of the surgical instrument of FIG. 4A.
Figure 4E:
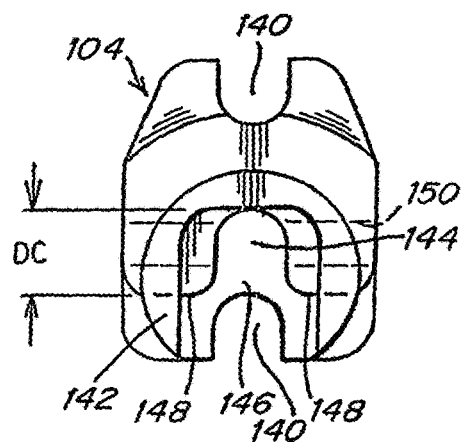
FIG. 4E is an end view of the nozzle alignment component of the surgical instrument of FIG. 4A, as viewed distally from a position proximal to the component.

In certain embodiments, especially those in which the evacuation lumen is shaped and positionable to enable evacuation of liquid and debris without the need for an external source of suction, evacuation efficiency can be enhanced by providing an enlargement in the internal diameter of the evacuation plumbing—for example in evacuation lumen 108 and/or between evacuation lumen 108 and evacuation tube 118—proximally of jet-receiving opening 126 and any optional constriction forming a venturi (not shown). In certain such embodiments, the inner diameter of the evacuation lumen and/or evacuation tube increases from a certain minimum value at a first, distal location to a certain maximum value at a more proximal location. More detail concerning the configuration of the evacuation lumen in such embodiments can be found in commonly-owned U.S. Pat. No. 6,375,635 and the U.S. Patent Publication No. 2003/0125660 A1. Such an expansion advantageously provides a diffuser element able to bring about the above-mentioned enhanced suction effect. In certain embodiments, such a diffuser may be provide by simply expanding the internal diameter of the evacuation lumen at some point along its length downstream of jet-receiving opening 126. In one such embodiment, such a diffuser may be effected by, for example, making the jet-receiving opening inner diameter somewhat smaller than the inner diameter of the evacuation lumen at any point downstream of the jet-receiving opening. In the above and/or other embodiments, an expansion can be provided by interconnecting the evacuation lumen to evacuation tubing 118 having a somewhat larger internal diameter than the evacuation lumen. An exemplary expansion of the evacuation line provided at an interconnection between the evacuation lumen and the evacuation tube could be provided by interconnecting an evacuation lumen having a selected internal diameter, for example of between about 0.1 inch and about 0.6 inch, with evacuation tubing having internal diameter exceeding that internal diameter of the evacuation lumen by about 5% to 150% percent, in certain embodiments between about 20% and 120%, depending on the degree of suction enhancement desired. The configuration of the illustrated embodiment of a nozzle alignment component 104 and the liquid jet-forming components at the distal end 103 of surgical instrument 100 are illustrated in greater detail in FIGS. 4C-4E. FIG. 4C illustrates distal end 103 of instrument 100 in cross section, and FIGS. 4D and 4E present more detailed views of nozzle alignment component 104. Referring now to FIG. 4C, distal tip 128 of pressure lumen 106, in the illustrated embodiment, includes nozzle assembly 70' described above in the context of FIG. 3B. As discussed above, the smoothly tapering shape of nozzle ring 21 of nozzle assembly 70' provides an enhanced vena contracta effect reducing or eliminating fluid pinch that can occur when fluid enters a sharp-edge constriction and does not follow the wall of the nozzle initially such that eddies can form between the outer streamlines and the nozzle wall, thereby decreasing efficiency. By contrast, by utilizing nozzle ring 21 of nozzle assembly 70' in surgical instrument 100, the streamlines of fluid flow tend to enter the nozzle smoothly and less energy is lost in eddies, leading to increased jet velocity, reduced pressure drop and increased collimation of liquid jet 130 formed by nozzle assembly 70'.

As mentioned above, when utilizing certain nozzle assembly configurations provided according to the invention, such as nozzle assembly 70' as illustrated in FIG. 4C, a liquid jet 130 can be formed that remains collimated over a substantially greater jet length JL than for typical conventional prior art nozzle surgical liquid jet instrument nozzle designs. For example, in certain embodiments of the invention, liquid jet instrument 100 utilizing nozzle assembly 70' including a nozzle ring 21 fabricated as described above in the context of FIGS. 1A-1E and having a jet opening diameter ND of about 0.0031 inch, can form and emit a liquid jet 130 that does not disperse to the point where a diameter of the expanded base of the jet 132 is three times as great as the initial diameter ND of the jet for at least about 0.75 inch at supply pressures ranging from about 3,000 psig to over 12,000 psig. This particular example corresponds to a cone angle (2×A as shown in FIG. 4C) of about 7.1 degrees. This cone angle is substantially less than, and the collimated jet length is substantially longer than, that achievable for a comparable, conventional, non-tapered nozzle having the same jet opening diameter (which would yield a liquid jet having a cone angle of about 20° or greater). In certain embodiments, liquid jet 130 formed by nozzle assembly 70' in liquid jet instrument 100 can have a cone angle less than 10 degrees, and in certain embodiments between 3 degrees and 6 degrees. This collimation allows the ability to provide longer liquid jet lengths JL than typically provided in conventional surgical liquid jet instruments, for example, liquid jet lengths not less than 5 mm, and certain embodiments not less than 10 mm, in certain embodiments between 10 mm and 20 mm, and in certain embodiments between 13 mm and 16 mm.

Although the semicircular cross-sectional profile of nozzle ring 21, described previously, is believed to be particularly efficient, in certain embodiments, significant improvement, over typical conventional surgical liquid jet nozzle designs, can be obtained utilizing other nozzle configurations in which a liquid flow passage through the nozzle has a diameter that continuously decreases along at least a portion of a liquid flow path through the nozzle. Such tapers can at least partially obviate the effects of flow path sharp edges. Such tapered nozzles can be produced by a variety of techniques, such as for example the above-mentioned photolithographic/electrodeposition technique, as well as by techniques such as micro-machining of blanks by various known micro machining methods, etc.

For certain embodiments of surgical instruments utilizing inventive nozzles and/or nozzle assemblies producing highly collimated jets, e.g. those producing a liquid jet having a cone angle less than about 10 degrees, the evacuation lumen 108 can be configured to have a somewhat different relationship of internal diameter to liquid jet dispersed diameter at the inlet to the evacuation lumen than has been described in Applicant's U.S. Pat. No. 6,375,635. Specifically, in such embodiments, when providing an evacuation lumen having a smallest internal diameter at the location of the jet-receiving opening, the jet-receiving opening can be sized so that it has a diameter of about 150% to 300% the diameter of a cross section of the base (e.g. 132) of the dispersed jet 130 as it crosses the plane defining the jet-receiving opening. In other such embodiments, not illustrated, in which an evacuation lumen having a smallest internal diameter at a location of a necked-down constriction at the distal end of the evacuation lumen is provided, the jet-receiving opening can be sized so that it has a diameter between about 150% to about 400%, the diameter of a cross-section of the base of the dispersed jet as it crosses the plane defining the jet-receiving opening, and the minimum opening of the constriction can be sized so that it has a diameter of between about 100% to about 200% the diameter of the cross-section of the base of the dispersed jet as it crosses the plane defining the minimum diameter opening of the constriction.

The configuration and function of an exemplary embodiment of a nozzle alignment component is now explained with reference to FIGS. 4C-4E. For embodiments of surgical liquid jet instruments, such as liquid jet instrument 100, providing an evacuation lumen 108, according to certain embodiments of the invention, an inventive nozzle alignment component 104 can be provided located at or near the distal end 103 of the instrument. The nozzle alignment component can be is configured and positioned to connect to the pressure lumen and, upon connection to the pressure lumen to align the nozzle with respect to the evacuation lumen so that the liquid jet enters the jet-receiving opening along a desired trajectory, when the instrument is in operation. As illustrated, nozzle alignment component 104 comprises an insert including a groove or channel 140 therein that is sized and configured to contain and secure a distal region of pressure lumen 106. Channel 140 may have a width and depth selected to mate with the outer diameter of high pressure lumen 106, such that the high pressure lumen can "snap into" the groove, thereby securely retaining and immobilizing the pressure lumen with respect to the component. In certain embodiments, the connection between the high pressure lumen and the alignment component 104 can be provided or enhanced by securing the high pressure lumen within groove 140 via other connection means, for example adhesives, welding, brazing, straps or clamps, etc.

Prior to fabrication, the distal end of the high pressure lumen can be bent, for example on a mandrel, and, upon fabrication, snapped into groove 140 of nozzle alignment component 104.

As illustrated, a proximal region of nozzle alignment component 104 comprising a downstream end of the insert, includes a section 142 that is sized and configured to be insertable into the jet receiving opening 126 of evacuation lumen 108. For example, the outer diameter of section 142 of alignment component 104 may be equal to or slightly greater than the inner diameter of the distal end of evacuation lumen 108. If necessary or desired, downstream evacuation lumen connecting component 142 of nozzle alignment component 104 can be secured within the distal end of evacuation tube 108 via any one of wide variety of suitable means that would be apparent to those skilled in the art. In one exemplary embodiment, a compression sleeve, not shown, may be provided to securely interconnect downstream portion 142 of alignment component 104 within the distal end of evacuation lumen 108.

In the particular exemplary embodiment illustrated, nozzle alignment component 104 further comprises therein an elongated jet interacting channel 144, having a depth DC (see FIG. 4E) and a length JL, wherein the liquid jet interacting channel 144 includes a longitudinally-oriented opening 146 to the surrounding environment extending along at least a portion of its length and, as is illustrated, along essentially the entire length, of the channel. Adjacent to the longitudinally-oriented jet interacting channel 144 are tissue contacting surfaces 148, which can be apposed to tissue within a surgical operating field during use of the instrument to facilitate the desired depth of cut. In addition, in the particular embodiment illustrated, one or more vent apertures 150 may be provided that are configured and positioned to provide fluid communication between an interior region of channel 144 and the surrounding environment when the longitudinally-oriented opening 146 of channel 144 is occluded by contact with tissue in the operating field during use. The particular function and advantage of providing such as jet-interacting channel is described in much greater detail in Applicant's U.S. Patent Publication No. 2003/0125660 A1, referred to above.

An alternative configuration of a nozzle alignment component is illustrated in FIGS. 5A and 5B and the distal portion of the pressure lumen mating with the nozzle alignment component, which distal portion of the pressure lumen is essentially identical to that illustrated above in FIG. 4C, is shown in FIGS. 5C and 5D. FIG. 5C illustrates the distal tip 128 of pressure lumen 106 prior to completion of formation of nozzle assembly 70', thus illustrating the appearance of holder 50 prior to insertion of nozzle ring 21 and the securing of the nozzle ring by crimping the distal tip of the pressure lumen, as is illustrated in the finished nozzle assembly 70' illustrated in FIG. 5B. Nozzle alignment component 104' is similar to nozzle alignment component 104 previously described except that the pressure lumen securing region of nozzle alignment component 104' positioned upstream of jet interacting channel 144 comprises a lumen 160, which completely surrounds the outer diameter of the distal portion 162 of pressure lumen 106 when the pressure lumen is inserted in to the nozzle alignment component 104'. During assembly of the distal end of an instrument including a nozzle component 104', pressure lumen 106 can be bent, on a mandrel, and, the bent distal portion of pressure lumen 106 can then be inserted into nozzle alignment component 104' by sliding the pressure lumen into groove 140 and lumen 160 in the direction of arrow 164.

Another alternative configuration for providing a distal end of a surgical liquid jet instrument providing a nozzle alignment component is illustrated in FIGS. 6A-6D. Nozzle alignment component 170 is integrally formed in a distal portion of evacuation lumen 108' itself. As such, alignment component 170 is configured and positioned to connect to distal region 162' of pressure lumen 106, but is integrally formed as part of the distal end of evacuation lumen 108', rather than being interconnected to the evacuation as was the case with the configurations previously illustrated hi FIGS. 4A-5D.

Nozzle alignment component 170 also illustrates an embodiment utilizing a nozzle assembly 70", previously illustrated and described in the context of FIG. 3C, in which liquid flow through the nozzle assembly tends to force nozzle ring 21 into sealing engagement with seating surfaces 58' of recessed well 54 of holder 50". As previously discussed, retaining element 78 as illustrated, need not be particularly mechanically strong or provide a particularly high level of restraining force. In the illustrated embodiment, retaining element 78 comprises a disk of a porous material, for example filter paper or filter media, inserted upstream of nozzle ring 21. Upon assembly in forming a functional surgical instrument including nozzle alignment component 170, distal region 162' of pressure lumen 106 would be inserted in to the distal end 172 of recessed well 54 and affixed and secured therein, for example by welding, brazing, solder, tubing fittings, etc. A jet interacting channel 144' having an opening 146' interacting with a surrounding atmosphere and tissue contacting surfaces 148' (FIG. 6C) can be fabricated from and evacuation lumen via cutting out a segment of the sidewall of the tubing comprising the evacuation lumen, as illustrated, or, in alternative embodiments, by forming a cavity in the side wall of the evacuation lumen by, for example pressing or stamping an indentation into the sidewall. Nozzle alignment component 170 and the nozzle assembly configuration and evacuation lumen configuration illustrated in FIGS. 6A-6D have the advantage of being simple in configuration and easy to manufacture, because few parts are required, and the configuration can be prepared by machining, casting, or other convenient fabrication methods.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. In cases where the present specification and a document incorporated by reference include conflicting disclosure, the present specification shall control.

What is claimed:

1. A surgical instrument comprising:
   a housing located at a distal end of the surgical instrument, the housing supporting a pressure lumen;
   the pressure lumen including a distal end mounted in a groove on an exterior surface of the housing;
   a nozzle positioned completely inside the distal end of the pressure lumen, the nozzle co-axial with the distal end of the pressure lumen and, in operation, co-axial with pressurized liquid flow passing through the nozzle, wherein the nozzle forms a tapered liquid flow passage with a diameter that continuously decreases along at least a portion of the liquid flow through the nozzle, and wherein the nozzle is formed as a torus with a flat surface and a curved opposite surface, the curved surface positioned upstream of the flat surface
   an evacuation lumen attached to a proximal end of the housing, the evacuation lumen comprising an opening at a distal end of the evacuation lumen opposite the nozzle, the opening configured to receive at least a portion of the liquid flow, the opening at least partially extending past the exterior of the housing,
   wherein the distal end of the pressure lumen extends beyond the distal end of the evacuation lumen such that, in operation, the received liquid flow is directed toward a proximal end of the surgical instrument.

2. The surgical instrument of claim 1 further including a handle located at a proximal end of the surgical instrument.

3. The surgical instrument of claim 1, wherein the distal end of the pressure lumen forms a recessed well in which the nozzle is retained and positioned.

4. The surgical instrument of claim 3, wherein the nozzle is secured and retained by the recessed well to sufficiently withstand an internal liquid pressure of at least about 1,000 psig without failure.

5. The surgical instrument of claim 3, wherein the recessed well includes an inner diameter greater than the outer diameter of the nozzle.

6. The surgical instrument of claim 3, further comprising a retaining element positioned in the recessed well configured to secure the nozzle in the recessed well.

7. The surgical instrument of claim 6, wherein the retaining element comprises at least one of: a ring press-fit into the recessed well, a weld, or a crimp in a wall of tubing comprising the recessed well.

8. The surgical instrument of claim 3, wherein the nozzle is press-fit into the recessed well.

9. The surgical instrument of claim 1, wherein, in operation, a liquid jet emitted from the nozzle has a cone angle between 3 degrees and 6 degrees.

10. The surgical instrument of claim 1, wherein, in operation, a liquid jet emitted by the nozzle has a cone angle not exceeding 10 degrees.

11. The surgical instrument of claim 1, wherein the pressure lumen is configured to convey a high-pressure liquid at a pressure of at least 1,000 psig.

12. The surgical instrument of claim 1, wherein the evacuation lumen is shaped and positioned to enable evacuation of the received liquid flow from the opening to a proximal end of the instrument.

13. The surgical instrument of claim 1, wherein the housing forms an angle with a portion of the pressure lumen.

14. The surgical instrument of claim 1, wherein the housing includes an elongated jet interacting channel.

15. The surgical instrument of claim 14, wherein the elongated jet interacting channel includes a longitudinally-oriented opening.

16. The surgical instrument of claim 1, further comprising at least one vent aperture extending through the housing.

17. The surgical instrument of claim 1, wherein the distal end of the pressure lumen forms a taper with a diameter that increases in a proximal direction.

18. The surgical instrument of claim 1, comprising a distal opening at the distal end of the pressure lumen, wherein a diameter of the distal opening is smaller than an outer diameter of the nozzle.

19. The surgical instrument of claim 1, wherein an inner diameter of the pressure lumen proximal to the nozzle is smaller than an outer diameter of the nozzle.

* * * * *